(12) United States Patent
Qiu et al.

(10) Patent No.: US 6,716,820 B1
(45) Date of Patent: Apr. 6, 2004

(54) 6-O-SUBSTITUTED BICYCLIC MACROLIDES

(75) Inventors: Yao-Ling Qiu, Andover, MA (US); Ly Tam Phan, Malden, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 10/455,001

(22) Filed: Jun. 5, 2003

(51) Int. Cl.[7] ............... A61K 31/70; C07H 17/08
(52) U.S. Cl. ............... 514/29; 536/7.2; 536/7.4
(58) Field of Search ............... 536/7.2, 7.4; 514/29

(56) References Cited

U.S. PATENT DOCUMENTS

| 5,866,549 | A | * | 2/1999 | Or et al. ............... 514/29 |
| 6,124,269 | A | | 9/2000 | Phan et al. ............... 514/29 |
| 6,399,582 | B1 | | 6/2002 | Hlasta et al. ............... 514/29 |

FOREIGN PATENT DOCUMENTS

| WO | WO 97/042205 A1 | 11/1997 | ............ C07H/17/08 |
| WO | WO 02/016380 A1 | 2/2002 | ............ C07H/17/08 |
| WO | WO 02/050091 A1 | 6/2002 | ............ C07H/17/08 |
| WO | WO 02/050092 A1 | 6/2002 | ............ C07H/17/08 |
| WO | WO 03/004509 A2 | 1/2003 | ............ C07H/17/08 |
| WO | WO 03/024986 A1 | 3/2003 | ............ C07H/17/08 |

OTHER PUBLICATIONS

Anhydrolide Macrolides. 1. Sythesis and Antibacterial Activity of 2,3–Anhydro–6–O–methyl 11,12–Carbamate Erythromycin A Analogs, Elliott et al, J. Med. Chem. 1998, 41, 1651–1659.

Anhydrolide Macrolides. 2. Sythesis and Antibacterial Activity of 2,3–Anhydro–6–O–methyl 11,12–Carbazate Erythromycin A Analogs, Griesgraber et al, J. Med. Chem. 1998, 41, 1660–1670.

* cited by examiner

*Primary Examiner*—Elli Peselev
(74) *Attorney, Agent, or Firm*—Jason D. Ferroue

(57) ABSTRACT

The present invention discloses compounds of formula I, or pharmaceutically acceptable salts, esters, or prodrugs thereof:

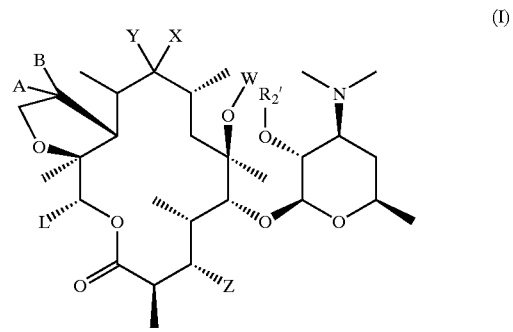

(I)

which exhibit antibacterial properties. The present invention further relates to pharmaceutical compositions comprising the aforementioned compounds for administration to a subject in need of antibiotic treatment. The invention also relates to methods of treating a bacterial infection in a subject by administering a pharmaceutical composition comprising the compounds of the present invention. The invention further includes process by which to make the compounds of the present invention.

9 Claims, No Drawings

6-O-SUBSTITUTED BICYCLIC MACROLIDES

REFERENCE TO RELATED APPLICATIONS

This application is related to commonly assigned U.S. patent applications, Ser. Nos. 10/455,219, 10/455,648 and 10/454,865 filed on even date herewith.

TECHNICAL FIELD

The present invention relates to novel semisynthetic macrolides having antibacterial activity and which are useful in the treatment and prevention of bacterial infections. More particularly, the invention relates to 11,12-cyclized erythromycin derivatives, compositions containing such compounds and methods for using the same, as well as processes for making such compounds.

BACKGROUND OF THE INVENTION

Erythromycins A through D, represented by formula (E) as illustrated below,

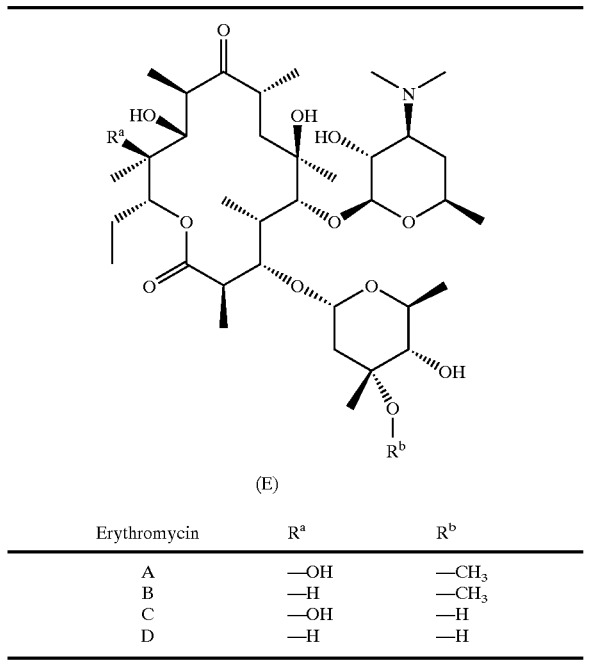

| Erythromycin | $R^a$ | $R^b$ |
|---|---|---|
| A | —OH | —$CH_3$ |
| B | —H | —$CH_3$ |
| C | —OH | —H |
| D | —H | —H | are well-known and potent antibacterial agents, used widely to treat and prevent bacterial infection. As with other antibacterials, however, bacterial strains having resistance or insufficient susceptibility to erythromycin have been identified. Also, erythromycin A has only weak activity against Gram-negative bacteria. Therefore, there is a continuing need to identify new erythromycin derivative compounds which possess improved antibacterial activity, which have less potential for developing resistance, which possess the desired Gram-negative activity, or which possess unexpected selectivity against target microorganisms. Consequently, numerous investigators have prepared chemical derivatives of erythromycin in an attempt to obtain analogs having modified or improved profiles of antibiotic activity.

Kashimura et al. have disclosed 6-O-methylerythromycin derivatives having a tricyclic basic nuclear structure in European Application 559896, published Nov. 11, 1991.

Also, Asaka et al. have disclosed 5-O-desoaminylerythronolide derivatives containing a tricyclic carbamate structure in PCT Application WO 93/21200, published Apr. 22, 1992.

Recently erythromycin derivatives containing a variety of substituents at the 6-O position have been disclosed in U.S. Pat. Nos. 5,866,549, 6,075,011 and 6,420,555 B1 as well as PCT Applications WO 00/78773 and WO 03/024986. Furthermore, Ma et. al. have described erythromycin derivatives with aryl groups tethered to the C-6 position in *J. Med Chem.*, 44, pp 4137–4156 (2001).

More recently, erythromycin derivatives containing a lactone moiety at the C11–C12 position have been disclosed in PCT Application WO 02/16380, published Feb. 28, 2002 as well as WO 02/50091 and WO 02/50092, both published Jun. 27, 2002 and WO 03/024986.

SUMMARY OF THE INVENTION

The present invention provides a novel class of C11–C12 cyclized erythromycin compounds that possess antibacterial activity.

In one aspect of the present invention there are disclosed novel bicyclic erythromycin compounds represented by formula I as illustrated below:

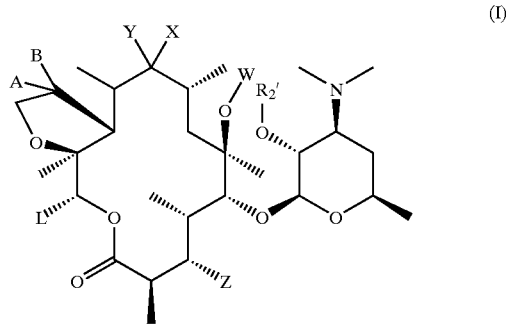

(I)

as well as the pharmaceutically acceptable salts, esters and prodrugs thereof.

In formula I:

A is selected from:
  (a) —OH;
  (b) —$OR_p$, where $R_p$ is a hydroxy protecting group;
  (c) —$R_1$, where $R_1$ is selected from:
    1. aryl;
    2. substituted aryl;
    3. heteroaryl; and
    4. substituted heteroaryl;
  (d) —$OR_1$, where $R_1$ is as previously defined;
  (e) —$R_2$, where $R_2$ is selected from:
    1. hydrogen;
    2. halogen;
    3. $C_1$–$C_6$ alkyl containing 0, 1, 2, or 3 heteroatoms selected O, S and N, optionally substituted with one or more substituents selected from halogen, cyano, oxo, aryl, substituted aryl, heteroaryl, and substituted heteroaryl;
    4. $C_2$–$C_6$ alkenyl containing 0, 1, 2, or 3 heteroatoms selected from O, S and N, optionally substituted with one or more substituents selected from halogen, cyano, oxo, aryl, substituted aryl, heteroaryl, and substituted heteroaryl; and
    5. $C_2$–$C_6$ alkynyl containing 0, 1, 2, or 3 heteroatoms selected from O, S and N, optionally substituted with one or more substituents selected from halogen, cyano, oxo, aryl, substituted aryl, heteroaryl, and substituted heteroaryl;
(f) —$OR_2$, where $R_2$ is previously defined;
(g) —$S(O)_nR_{11}$, where n=0, 1 or 2, and $R_{11}$ is selected from hydrogen, $R_1$ and $R_2$, where $R_1$ and $R_2$ are as previously defined;
(h) —$OC(O)R_{11}$, where $R_{11}$ is as previously defined;
(i) —$C(O)R_{11}$, where $R_{11}$ is as previously defined;
(j) —$C(O)NHR_{11}$, where $R_{11}$ is as previously defined;
(k) —$OC(O)NHR_{11}$, where $R_{11}$ is as previously defined;
(l) —$NHC(O)R_{11}$, where $R_{11}$ is as previously defined;
(m) —$NHC(O)NHR_{11}$, where $R_{11}$ is as previously defined;
(n) —$NHS(O)_nR_{11}$, where n and $R_{11}$ are as previously defined;
(o) —$NR_{14}R_{15}$, where $R_{14}$ and $R_{15}$ are each independently $R_{11}$, where $R_{11}$ is as previously defined; and
(p) —$NHR_3$, where $R_3$ is an amino protecting group;
B is selected from:
(a) hydrogen;
(b) deuterium;
(c) —CN;
(d) —$NO_2$;
(e) halogen;
(f) —OH;
(g) —$R_1$, where $R_1$ is as previously defined;
(h) —$R_2$, where $R_2$ is as previously defined; and
(i) —$OR_p$, where $R_p$ is as previously defined;
provided that when B is halogen, —$NO_2$, —OH or $OR_p$, A is $R_1$ or $R_2$;
or, alternatively, A and B taken together with the carbon atom to which they are attached are selected from:
(a) C=O;
(b) $C(OR_2)_2$, where $R_2$ is as previously defined;
(c) $C(SR_2)_2$, where $R_2$ is as previously defined;
(d) $C(OR_{12})(OR_{13})$, where $R_{12}$ and $R_{13}$ taken together are —$(CH_2)_m$—, and where m=2 or 3;
(e) $C(SR_{12})(SR_{13})$, wher $R_{12}$ and $R_{13}$ taken together are —$(CH_2)_m$— and where m is as previously defined,
(f) C=$CR_{11}R_{14}$, where $R_{11}$ and $R_{14}$ are as previously defined;
(g) C=N—O—$OR_{11}$, where $R_{11}$ is as previously defined;
(h) C=$NNHR_{11}$, where $R_{11}$ is as previously defined;
(i) C=$NNHC(O)R_{11}$, where $R_{11}$ is as previously defined;
(j) C=NN=$CR_{11}R_{14}$, where $R_{11}$ and $R_{14}$ are as previously defined;
(k) C=$NNHC(O)NHR_{11}$, where $R_{11}$ is as previously defined;
(l) C=$NNHS(O)_nR_{11}$, where n and $R_{11}$ areas previously defined;
(m) C=$NNHR_3$, where $R_3$ is as previously defined; and
(n) C=$NR_{11}$, where $R_{11}$ is as previously defined;
one of X and Y is hydrogen and the other is selected from:
(a) hydrogen;
(b) deuterium;
(c) —OH;
(d) —$OR_p$, where $R_p$ is as previously defined; and
(e) —$NR_4R_5$, where $R_4$ and $R_5$ are each independently selected from:
1. hydrogen; and
2. $C_1$–$C_{12}$ alkyl, optionally substituted with one or more substituents selected from halogen, cyano, aryl, substituted aryl, heteroaryl and substituted heteroaryl; or $R_4$ and $R_5$, taken together with the nitrogen atom to which they are attached form a 3–10 membered heteroalkyl ring containing 0–2 additional hetero atoms selected from O, S and N; or alternatively, X and Y taken together with the carbon atom to which they are attached are selected from:
(a) C=O;
(b) C=$NR_{11}$, where $R_{11}$ is as previously defined;
(c) C=$NC(O)R_{11}$, where $R_{11}$ is as previously defined;
(d) C=N—$OR_6$, where $R_6$ is selected from:
1. hydrogen;
2. —$CH_2O(CH_2)_2OCH_3$,
3. —$CH_2O(CH_2O)_nCH_3$, where n is as previously defined;
4. —$C_1$–$C_{12}$ alkyl, optionally substituted with one or more substituents selected from the group consisting of halogen, cyano, aryl, substituted aryl, heteroaryl and substituted heteroaryl;
5. $C_3$–$C_{12}$ cycloalkyl;
6. C(O)—$C_1$–$C_{12}$ alkyl;
7. C(O)—$C_3$–$C_{12}$ cycloalkyl;
8. C(O)—$R_1$, where $R_1$ is as previously defined; and
9. —$Si(R_a)(R_b)(R_c)$, wherein $R_a$, $R_b$ and $R_c$ are each independently selected from $C_1$–$C_{12}$ alkyl, aryl and substituted aryl; and
(e) C=N—O—$C(R_7)(R_8)$—O—$R_6$, where $R_6$ is as previously defined, provided that $R_6$ is not C(O)—$C_1$–$C_{12}$ alkyl, C(O)—$C_3$–$C_{12}$ cycloalkyl, or C(O)—$R_1$; and $R_7$ and $R_8$ taken together with the carbon atom to which they are attached form a $C_3$–$C_{12}$ cycloalkyl group or each is independently selected from:
1. hydrogen; and
2. $C_1$–$C_{12}$ alkyl;
L is selected from:
(a) —$CH(OH)CH_3$;
(b) $C_1$–$C_6$ alkyl, optionally substituted with one or more substituents selected from halogen, cyano, aryl, substituted aryl, heteroaryl, and substituted heteroaryl;
(c) $C_2$–$C_6$ alkenyl, optionally substituted with one or more substituents selected from halogen, cyano, aryl, substituted aryl, heteroaryl, and substituted heteroaryl; and
(d) $C_2$–$C_6$ alkynyl, optionally substituted with one or more substituents selected from halogen, cyano, aryl, substituted aryl, heteroaryl, and substituted heteroaryl;
W is selected from:
(a) $C_2$–$C_6$ alkyl containing 0, 1, 2, or 3 heteroatoms selected from O, S and N, optionally substituted with one or more substituents selected from halogen, cyano, oxo, aryl, substituted aryl, heteroaryl, and substituted heteroaryl;
(b) $C_2$–$C_6$ alkenyl containing 0, 1, 2, or 3 heteroatoms selected from O, S and N, optionally substituted with one or more substituents selected from halogen, cyano, oxo, aryl, substituted aryl, heteroaryl, and substituted heteroaryl; and
(c) $C_2$–$C_6$ alkynyl containing 0, 1, 2, or 3 heteroatoms selected from O, S and N, optionally substituted with one or more substituents selected from halogen, cyano, oxo, aryl, substituted aryl, heteroaryl, and substituted heteroaryl;

Z is selected from:
(a) hydrogen;
(b) —OH;
(c) —$OR_p$, where $R_p$ is as previously defined;
(d) —$OR_{11}$, where $R_{11}$ is as previously defined;
(e) —$OC(O)R_{11}$, where $R_{11}$ is as previously defined;
(f) —$OC(O)NHR_{11}$, where $R_{11}$ is as previously defined;
(g) —$S(O)_nR_{11}$, where n and $R_{11}$ are as previously defined;
(h) —

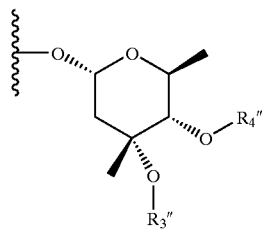

where $R_3''$ is hydrogen or methyl; $R_4''$ is hydrogen or $R_p$, where $R_p$ is as previously defined; and
$R_2'$ is hydrogen or $R_p$, where $R_p$ is as previously defined.

In another aspect of the present invention there are disclosed pharmaceutical compositions comprising a therapeutically effective amount of a compound of the invention in combination with a pharmaceutically acceptable carrier, and treatment of antibacterial infections with such compositions. Suitable carriers and methods of formulation are also disclosed. The compounds and compositions of the present invention have antibacterial activity.

In a further aspect of the present invention there are provided processes for the preparation of 11, 12-cyclized erythromycin derivatives of formula (I).

DETAILED DESCRIPTION OF THE INVENTION

A first embodiment of the present invention includes compounds represented by formula I, as illustrated above, as well as the pharmaceutically acceptable salts, esters and prodrugs thereof.

A preferred group of compounds of the present invention are those represented by the formula

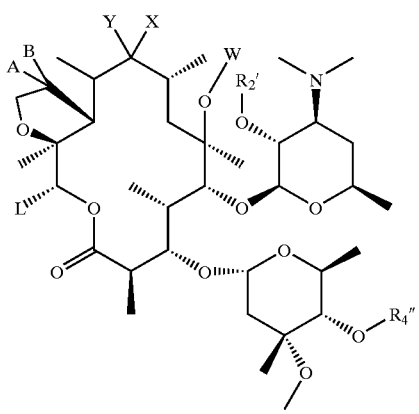

(II)

where A, B, L, W, X, Y, $R_4''$ and $R_2'$ are as previously defined.

Another preferred group of compounds of the present invention are those represented by formula I wherein L is ethyl and A, B, W, X, Y, Z and $R_2'$ are as previously defined.

Representative compounds of the invention are those selected from:

Compound of formula II: A and B taken together with the carbon atom to which they are attached are C=$CH_2$, L is $CH_2CH_3$, W is $CH_2CH$=$CH_2$, X and Y taken together with the carbon atom to which they are attached are C=O, $R_4''$ is $C(O)CH_3$, and $R_2'$ is H;

Compound of formula II: A and B taken together with the carbon atom to which they are attached are C=$CH_2$, L is $CH_2CH_3$, W is $CH_2CH$=$CH_2$, X and Y taken together with the carbon atom to which they are attached are C=O, $R_4''$ is H and $R_2'$ is H;

Compound of formula I: A and B taken together with the carbon atom to which they are attached are C=$CH_2$, L is $CH_2CH_3$, W is $CH_2CH$=$CH_2$, X and Y taken together with the carbon atom to which they are attached are C=O, Z is OH and $R_2'$ is H;

Compound of formula I: A and B taken together with the carbon atom to which they are attached are C=$CH_2$, L is $CH_2CH_3$, W is $CH_2CH$=$CH_2$, X and Y taken together with the carbon atom to which they are attached are C=O, Z is OH and $R_2'$ is H;

Compound of formula II: A and B taken together with the carbon atom to which they are attached are C=$CH_2$, L is $CH_2CH_3$, W is $CH_2CH(O)$, X and Y taken together with the carbon atom to which they are attached are C=O, $R_2'$ is H, and $R_4''$ is H;

Compound of formula II: A and B taken together with the carbon atom to which they are attached are C=$CH_2$, L is $CH_2CH_3$, W is $CH_2C$≡CH, X and Y taken together with the carbon atom to which they are attached are C=O, $R_2'$ is H, and $R_4''$ is H;

Compound of formula II: A and B taken together with the carbon atom to which they are attached are C=$CH_2$, L is $CH_2CH_3$, W is $CH_2C$≡C-(3-quinolyl), X and Y taken together with the carbon atom to which they are attached are C=O, $R_2'$ is H, and $R_4''$ is H;

Compound of formula II: A and B taken together with the carbon atom to which they are attached are C=$CH_2$, L is $CH_2CH_3$, W is $CH_2CH_2NHCH_2$-(4-chlorophenyl), X and Y taken together with the carbon atom to which they are attached are C=O, $R_2'$ is H, and $R_4''$ is H;

Compound of formula II: A and B taken together with the carbon atom to which they are attached are C=$CH_2$, L is $CH_2CH_3$, W is $CH_2CH_2NCH_3CH_2$-phenyl, X and Y taken together with the carbon atom to which they are attached are C=O, $R_2'$ is H, and $R_4''$ is H;

Compound of formula II: A and B taken together with the carbon atom to which they are attached are C=$CH_2$, L is $CH_2CH_3$, W is $CH_2CH_2NCH_3CH_2$-(2-pyridyl), X and Y taken together with the carbon atom to which they are attached are C=O, $R_2'$ is H, and $R_4''$ is H;

Compound of formula II: A and B taken together with the carbon atom to which they are attached are C=$CH_2$, L is $CH_2CH_3$, W is $CH_2CH_2NCH_3CH_2$-(3-pyridyl), X and Y taken together with the carbon atom to which they are attached are C=O, $R_2'$ is H, and $R_4''$ is H;

Compound of formula II: A and B taken together with the carbon atom to which they are attached are C=$CH_2$, L is $CH_2CH_3$, W is $CH_2CH_2NCH_3CH_2$-(3-quinolyl), X and Y taken together with the carbon atom to which they are attached are C=O, $R_2'$ is H, and $R_4''$ is H;

Compound of formula II: A and B taken together with the carbon atom to which they are attached are C=$CH_2$, L is $CH_2CH_3$, W is $CH_2CH$=CH-phenyl, X and Y taken together with the carbon atom to which they are attached are C=O, $R_2'$ is H, and $R_4''$ is H;

Compound of formula II: A and B taken together with the carbon atom to which they are attached are C=CH$_2$, L is CH$_2$CH$_3$, W is CH$_2$CH=CH-(2-pyridyl), X and Y taken together with the carbon atom to which they are attached are C=O, $R_2'$ is H, and $R_4''$ is H;

Compound of formula II: A and B taken together with the carbon atom to which they are attached are C=CH$_2$, L is CH$_2$CH$_3$, W is CH$_2$CH=CH-(3-pyridyl), X and Y taken together with the carbon atom to which they are attached are C=O, $R_2'$ is H, and $R_4''$ is H;

Compound of formula II: A and B taken together with the carbon atom to which they are attached are C=CH$_2$, L is CH$_2$CH$_3$, W is CH$_2$CH=CH-(3-(5-cyano)pyridyl), X and Y taken together with the carbon atom to which they are attached are C=O, $R_2'$ is H, and $R_4''$ is H;

Compound of formula II: A and B taken together with the carbon atom to which they are attached are C=CH$_2$, L is CH$_2$CH$_3$, W is CH$_2$CH=CH-(6-(aminocarbonyl)-3-quinolyl), X and Y taken together with the carbon atom to which they are attached are C=O, $R_2'$ is H, and $R_4''$ is H;

Compound of formula II: A and B taken together with the carbon atom to which they are attached are C=CH$_2$, L is CH$_2$CH$_3$, W is CH$_2$C≡C-phenyl, X and Y taken together with the carbon atom to which they are attached are C=O, $R_2'$ is H, and $R_4''$ is H;

Compound of formula II: A and B taken together with the carbon atom to which they are attached are C=CH$_2$, L is CH$_2$CH$_3$, W is CH$_2$C≡C-(2-pyridyl), X and Y taken together with the carbon atom to which they are attached are C=O, $R_2'$ is H, and $R_4''$ is H;

Compound of formula II: A and B taken together with the carbon atom to which they are attached are C=CH$_2$, L is CH$_2$CH$_3$, W is CH$_2$C≡C-(3-pyridyl), X and Y taken together with the carbon atom to which they are attached are C=O, $R_2'$ is H, and $R_4''$ is H;

Compound of formula II: A and B taken together with the carbon atom to which they are attached are C=CH$_2$, L is CH$_2$CH$_3$, W is CH$_2$C≡C-(3-(5-cyano)pyridyl), X and Y taken together with the carbon atom to which they are attached are C=O, $R_2'$ is H, and $R_4''$ is H;

Compound of formula II: A and B taken together with the carbon atom to which they are attached are C=CH$_2$, L is CH$_2$CH$_3$, W is CH$_2$C≡C-(5-(2-pyridyl)-2-thienyl), X and Y taken together with the carbon atom to which they are attached are C=O, $R_2'$ is H, and $R_4''$ is H;

Compound of formula II: A and B taken together with the carbon atom to which they are attached are C=CH$_2$, L is CH$_2$CH$_3$, W is CH$_2$C≡C-(5-(3-pyridinyl)-2-pyrrolyl), X and Y taken together with the carbon atom to which they are attached are C=O, $R_2'$ is H, and $R_4''$ is H;

Compound of formula II: A and B taken together with the carbon atom to which they are attached are C=CH$_2$, L is CH$_2$CH$_3$, W is CH$_2$C≡C-(5-(2-pyrimidyl)-2-thienyl), X and Y taken together with the carbon atom to which they are attached are C=O, $R_2'$ is H, and $R_4''$ is H;

Compound of formula II: A and B taken together with the carbon atom to which they are attached are C=CH$_2$, L is CH$_2$CH$_3$, W is CH$_2$C≡C-(5-(2-pyrazinyl)-2-pyrrolyl), X and Y taken together with the carbon atom to which they are attached are C=O, $R_2'$ is H, and $R_4''$ is H; or Compound of formula II: A and B taken together with the carbon atom to which they are attached are C=CH$_2$, L is CH$_2$CH$_3$, W is CH$_2$C≡C-(6-quinolyl), X and Y taken together with the carbon atom to which they are attached are C=O, $R_2'$ is H, and $R_4''$ is H.

Definitions

The terms "$C_1$–$C_3$ alkyl," "$C_1$–$C_6$ alkyl" or "$C_1$–$C_{12}$ alkyl," as used herein, refer to saturated, straight- or branched-chain hydrocarbon radicals containing between one and three, one and six, or one and twelve carbon atoms, respectively. Examples of $C_1$–$C_3$ alkyl radicals include methyl, ethyl, propyl and isopropyl radicals; examples of $C_1$–$C_6$ alkyl radicals include, but are not limited to, methyl, ethyl, propyl, isopropyl, n-butyl, tert-butyl, neopentyl and n-hexyl radicals; and examples of $C_1$–$C_{12}$ alkyl radicals include, but are not limited to, methyl, ethyl, n-propyl, isopropyl, n-hexyl, n-octyl, n-decyl and n-dodecyl radicals.

The terms "$C_2$–$C_6$ alkenyl" or "$C_2$–$C_{12}$ alkenyl," as used herein, denote a monovalent group derived from a hydrocarbon moiety containing from two to six or two to twelve carbon atoms having at least one carbon-carbon double bond by the removal of a single hydrogen atom. Alkenyl groups include, but are not limited to, ethenyl, propenyl, isobutenyl, 1,3-hexadienyl, n-hexenyl, 3-pentenyl, 1-methyl-2-buten-1-yl, and the like.

The terms "$C_2$–$C_6$ alkynyl" or "$C_2$–$C_{12}$ alkynyl," as used herein, denote a monovalent group derived from a hydrocarbon moiety containing from two to six or two to twelve carbon atoms having at least one carbon-carbon triple bond by the removal of two hydrogen atoms. Representative alkynyl groups include, but are not limited to, ethynyl, 1-propynyl, 1-butynyl, isopentynyl, 1,3-hexadiynyl, n-hexynyl, 3-pentynyl, 1-hexen-3-ynyl and the like.

The terms "halo" and "halogen," as used herein, refer to an atom selected from fluorine, chlorine, bromine and iodine.

The term "haloalkyl" denotes an alkyl group, as defined above, having one, two or three halogen atoms attached thereto and is exemplified by such groups as chloromethyl, bromoethyl, trifluoromethyl, and the like.

The term "aryl," as used herein, refers to a mono-, bicyclic or tricyclic carbocyclic ring system having one, two or three aromatic rings including, but not limited to, phenyl, naphthyl, anthryl, azulyl, tetrahydronaphthyl, indanyl, indenyl and the like.

The term "substituted aryl," as used herein, refers to an aryl group, as defined herein, substituted by independent replacement of one or more of the hydrogen atoms thereon with substituents independently selected from substituents such as, but not limited to, alkyl, haloalkyl, alkoxy, thioalkoxy, amino, alkylamino, dialkylamino, acylamino, hydroxy, cyano, halo. mercapto, nitro, carboxaldehyde, carboxyl, alkoxycarbonyl, carboxamide, aryl, substituted aryl, heteroaryl, substituted heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, thio, aryl-thio, heteroarylthio, benzyl-thio, $C_1$–$C_6$-alkyl-thio, or methylthiomethyl. Representative substituents include, but are not limited to, F, Cl, Br, I, OH, NO$_2$, CN, C(O)—$C_1$–$C_6$-alkyl, C(O)-aryl, C(O)-heteroaryl, CO$_2$-alkyl, CO$_2$-aryl, CO$_2$-heteroaryl, CONH$_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, OCO$_2$-alkyl, OCO$_2$-aryl, OCO$_2$-heteroaryl, OCONH$_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, tetrafluorophenyl and pentafluorophenyl The term "heteroaryl," as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "substituted heteroaryl," as used herein, refers to a heteroaryl group as defined herein, substituted by independent replacement of one, or more of the hydrogen atoms thereon with substituents independently selected from substituents such as, but not limited to, alkyl, haloalkyl, alkoxy, thioalkoxy, amino, alkylamino, dialkylamino, acylamino, hydroxy, cyano, halo, mercapto, nitro, carboxaldehyde, carboxyl, alkoxycarbonyl, carboxamide, aryl, substituted aryl, heteroaryl, substituted heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, thio, aryl-thio, heteroarylthio, benzyl-thio, $C_1$–$C_6$-alkyl-thio, or methylthiomethyl. Representative substituents include, but are not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, tetrafluorophenyl and pentafluorophenyl.

The term "$C_3$–$C_{12}$-cycloalkyl", as used herein, denotes a monovalent group derived from a monocyclic or bicyclic saturated carbocyclic ring compound having from 3 to 12 carbon atoms by the removal of a single hydrogen atom. Examples include, but not limited to, cyclopropyl, cyclobutyl, cyclopentyl, cyclohexyl, bicyclo [2.2.1] heptyl, and bicyclo [2.2.2] octyl.

The term "substituted $C_3$–$C_{12}$-cycloalkyl", as used herein, refers to a $C_3$–$C_{12}$-cycloalkyl group, as defined herein, substituted by independent replacement of one or more of the hydrogen atoms therein with substituents independently selected from substituents such as, but not limited to, alkyl, haloalkyl, alkoxy, thioalkoxy, amino, alkylamino, dialkylamino, acylamino, hydroxy, cyano, halo, mercapto, nitro, carboxaldehyde, carboxyl, alkoxycarbonyl, carboxamide, aryl, substituted aryl, heteroaryl, substituted heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, thio, aryl-thio, heteroarylthio, benzyl-thio, $C_1$–$C_6$-alkyl-thio, or methylthiomethyl. Representative substituents include, but are not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, tetrafluorophenyl and pentafluorophenyl The term "$C_1$–$C_3$-alkyl-$C_3$–$C_5$-cycloalkyl", as used herein, refers to a $C_3$–$C_5$ cycloalkyl radical, as defined herein, attached to a $C_1$–$C_3$-alkyl radical by replacement of a hydrogen atom on the latter.

The term "heterocycloalkyl," as used herein, refers to a non-aromatic 3-, 4-, 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "substituted heterocycloalkyl", as used herein, refers to a cycloalkyl group, as gefined herein, substituted by independent replacement of one or more of the hydrogen atoms therein with substituents independently selected from substituents such as, but not limited to, alkyl, haloalkyl, alkoxy, thioalkoxy, amino, alkylamino, dialkylamino, acylamino, hydroxy, cyano, halo, mercapto, nitro, carboxaldehyde, carboxyl, alkoxycarbonyl, carboxamide, aryl, substituted aryl, heteroaryl, substituted heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, thio, aryl-thio, heteroarylthio, benzyl-thio, $C_1$–$C_6$-alkyl-thio, or methylthiomethyl. Representative substituents include, but are not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CH_2Cl_2$, $CH_2OH$, $CH_2CH_2OH$, $CH_2NH_2$, $CH_2SO_2CH_3$, tetrafluorophenyl and pentafluorophenyl The term "heterocyclic", as used herein, refers to heterocycloalkyl and heteroaryl. The term "substituted heterocyclic", as used herein, refers to substituted heterocycloalkyl and substituted heteroaryl.

The term "$C_1$–$C_6$ alkoxy", as used herein, refers to a $C_1$–$C_6$ alkyl group, as previously defined, attached to the parent molecular moiety through an oxygen atom. Examples of $C_1$–$C_6$-alkoxy include, but are not limited to, methoxy, ethoxy, propoxy, isopropoxy, i-butoxy, zert-butoxy, neopentoxy and n-hexoxy.

The term "$C_1$–$C_3$-alkylamino", as used herein, refers to one or two $C_1$–$C_3$-alkyl groups, as previously defined, attached to the parent molecular moiety through a nitrogen atom. Examples of $C_1$–$C_3$-alkylamino include, but are not limited to, methylamino, dimethylainino, ethylamino, diethylamino, and propylamino.

The term "alkylamino" refers to a group having the structure —NH($C_1$–$C_{12}$ alkyl) where $C_1$–$C_{12}$ alkyl is as previously defined.

The term "dialkylamino" refers to a group having the structure —N($C_1$–$C_{12}$ alkyl) ($C_1$–$C_{12}$ alkyl), where $C_1$–$C_{12}$ alkyl is as previously defined. Examples of dialkylamino are, but not limited to, dimethylamino, diethylamino, methylethylamino, piperidino, and the like.

The term "alkoxycarbonyl" represents an ester group, i.e. an alkoxy group, attached to the parent molecular moiety through a carbonyl group such as methoxycarbonyl, ethoxycarbonyl, and the like.

The term "carboxaldehyde", as used herein, refers to a group of formula —CHO.

The term "carboxy", as used herein, refers to a group of formula —COOH.

The term "carboxamide", as used herein, refers to a group of formula —C(O)NH($C_1$–$C_{12}$ alkyl) or —C(O)N($C_1$–$C_{12}$ alkyl) ($C_1$–$C_{12}$ alkyl).

"Hydroxy protecting group", as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf, for example, T. H. Greene and P. G. M. Wuts, *Protective Groups in Organic Synthesis*, 3rd edition, John Wiley & Sons, New York (1999). Examples of hydroxy protecting groups include, but are not limited to, methylthiomethyl, tert-dimethylsilyl, tert-butyidiphenylsilyl, acyl substituted with an aromatic group and the like.

The term "protected hydroxy" refers to a hydroxy group protected with a hydroxy protecting group, as defined above, including benzoyl, acetyl, trimethylsilyl, triethylsilyl, methoxymethyl groups, for example.

"Aldehyde-protecting group", as used herein, refers to an easily removable group which is known to protect an aldehyde group against undesirable reaction during synthetic procedures and to be selectively removable. The use of aldehyde-protecting groups is well known in the art for protecting aldehyde groups against undesirable reactions during a synthetic procedure and many such protecting groups are known. See, for example, T. H. Greene and P. G. M. Wuts, *Protective Groups in Organic Synthesis*, op. cit. Examples of aldehyde-protecting groups include, but are not limited to, acetals, ketals, O-substituted cyanohydrins, substituted hydrazones, imines and the like.

The term "protected aldehyde", as used herein, refers to an aldehyde group protected with an aldehyde-protecting group, as defined above, including dimethyl acetyl, 1,3-dioxolane, 1,3-dioxane an the like.

"Amino-protecting group", as used herein, refers to an easily removable group which is known in the art to protect an amino group against undesirable reaction during synthetic procedures and to be selectively removable. The use of amino-protecting groups is well known in the art for protecting groups against undesirable reactions during a synthetic procedure and many such protecting groups are known, cf. for example, T. H. Greene and P. G. M. Wuts, *Protective Groups in Organic Synthesis*, op. Cit. Examples of amino protecting groups include, but are not limited to, 9-fluorenylmethyl carbamate, benzyl carbonate, tert-butyl carbonate, benzyl, p-toluene sulfonyl, acyl and the like.

The term "protected amino", as used herein, refers to an amino group protected by an amino-protecting group, as defined herein.

The term "aprotic solvent", as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

The term "protogenic organic solvent", as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present. Further, in those cases where a bond between carbon atoms of the macrolide is a double bond both the cis and trans forms are within the scope of the invention described in this application.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs", as used herein, refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. The term "prodrug" refers to compounds that are rapidly transformed in vivo to yield the parent compound of the above formula, for example by hydrolysis in blood. A thorough discussion is provided in T. Higuchi and V. Stella, "Pro-drugs as Novel Delivery Systems, Vol. 14 of the ACS Symposium Series, and in Edward B. Roche, ed., "Bioreversible Carriers in Drug Design", American Pharmaceutical Association and Pergamon Press, 1987, both of which are incorporated herein by reference.

Antibacterial Activity

Susceptibility tests can be used to quantitatively measure the in vitro activity of an antimicrobial agent against a given bacterial isolate. Compounds were tested for in vitro antibacterial activity by a micro-dilution method. Minimal Inhibitory Concentration (MIC) was determined in 96 well microtiter plates utilizing the appropriate Mueller Hinton Broth medium (CAMHB) for the observed bacterial isolates. Antimicrobial agents were serially diluted (2-fold) in DMSO to produce a concentration range from about 64 $\mu$g/ml to about 0.03 $\mu$g/ml. The diluted compounds (2 $\mu$l/well) were then spotted to sterile 96-well microtiter plates. The inoculum for each bacterial strain was adjusted to $5.5 \times 10^5$ CFU/ml in appropriate MIC medium; 200 ul/well of this inoculum was added to the 96-well microtiter plate resulting in a final concentration of $1 \times 10^5$ CFU/ml. The 96 well plates were covered and incubated in a humidified atmosphere at 35+/-2° C. for 16–24 hours depending on the bacterial strain tested. Following incubation, plate wells were visually examined by Optical Density measurement for the presence of growth (turbidity). The lowest concentration of an antimicrobial agent at which no visible growth occurs was defined as the MIC. The compounds of the invention generally demonstrated an MIC in the range from about 64 $\mu$g/ml to about 0.03 $\mu$g/ml.

All in vitro testing follows the guidelines described in the Approved Standards M7-A5 protocol, published by the National Committee for Clinical Laboratory Standards (NCCLS).

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such asethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracistemally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethyl cellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or other animal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other animal in single or in divided doses can be in amounts, for example, from 0.01 to about 50 mg/kg body weight or more usually from 0.1 to about 25 mg/kg body weight. Single dose compositions may contain such amounts or submultiples thereof to make up the daily dose. In general, treatment regimens according to the present invention comprise administration to a patient in need of such treatment of from about 10 mg to about 1000 mg of the compound(s) of this invention per day in single or multiple doses.

The pharmaceutical compositions of this invention can be administered to fish by blending them in the fish feed to be administered orally or may be dissolved in water in which sick fish are placed to swim around (a method using a so-called "medicated bath"). The dosage for the treatment of fish differs depending upon the purpose of administration (prevention or cure of disease) and type, size and extent of infection of the fish to be treated. Generally, a dosage of 5–1000 mg, preferably 20–100 mg, per kg of body weight of fish may be administered per day, either at one time or divided into several times. It will be recognized that the above-specified dosage is only a general range which may be reduced or increased depending on the age, body weight, condition of disease, etc. of the fish.

Abbreviations

Abbreviations which may be used in the descriptions of the schemes and the examples that follow are: Ac for acetyl; AIBN for 2,2-azobisisobutyronitrile; Bn for benzyl; Boc for 1-butoxycarbonyl; Bu3SnH for tributyltin hydride; Bz for benzoyl; CDI for carbonyidiimidazole; dba for dibenzylidene acetone; dppb for diphenylphosphino butane; DBU for 1,8-diazabicyclo [5.4.0]undec-7-ene; DCC for 1,3-dicyclohexylcarbodiimide; DEAD for diethylazodicarboxylate; DIBAL-H for diisopropyl aluminum hydride; DIC for 1,3-diisopropylcarbodiimide; DIEA for diisopropylethylamine; DMAP for dimethylaminopyridine; DMF for dimethyl formamide; DMSO for dimethylsulfoxide; DPPA for diphenylphosphoryl azide; LAH for lithium aluminum hydride; EtOAc for ethyl acetate; KHMDS for potassium bis (trimethylsilyl) amide; LDA for lithium diisopropyl amide; MeOH for methanol; Me$_2$S for dimethyl sulfide; MOM for methoxymethyl; OMs for mesylate; OTos for tosylate; NaN (TMS)$_2$ for sodium bis(trimethylsilyl)amide; NCS for N-chlorosuccinimide; NMMO for 4-methylmorpholine N-oxide; PCC for pyridinium chlorochromate; PDC for pyridinium dichromate; Ph for phenyl; POPd for dihydrogen dichlorobis(di-tert-butylphosphino)palladium(II); TEA for triethylamine; THF for tetrahydrofuran; TPP or PPh$_3$ for triphenylphosphine; TBS for tert-butyl dimethylsilyl; and TMS for trimethylsilyl.

Synthetic Methods

The compounds and processes of the present invention will be better understood in connection with the following synthetic schemes which are illustrative of the methods by which the compounds of the invention may be prepared. The groups A, B, W, X, Y, Z, R$_2$', R$_4$" and R$_{11}$ are as previously defined unless otherwise noted below.

A preferred intermediate for the preparation of compounds represented by formula I is a compound represented by formula III as illustrated below:

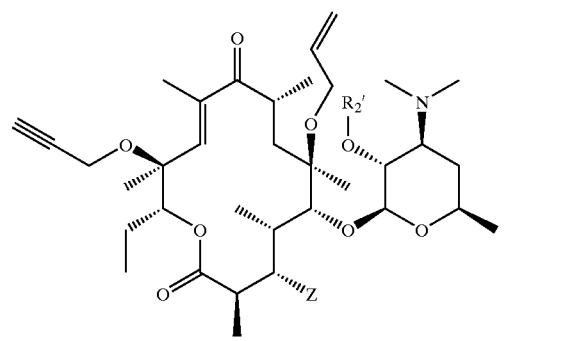

(III)

where R$_2$' and Z are as previously defined.

Another preferred intermediate for the preparation of compounds represented by formula I is a compound represented by formula IV as illustrated below:

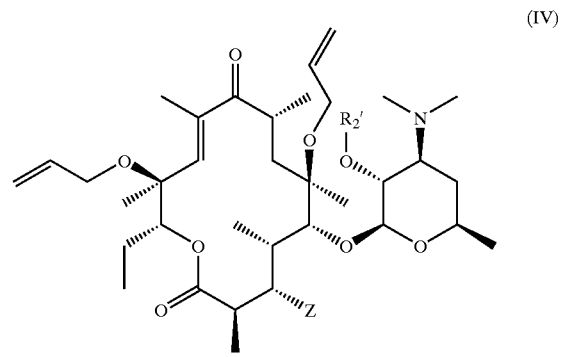

(IV)

where R$_2$' and Z are as previously defined.

Scheme 1
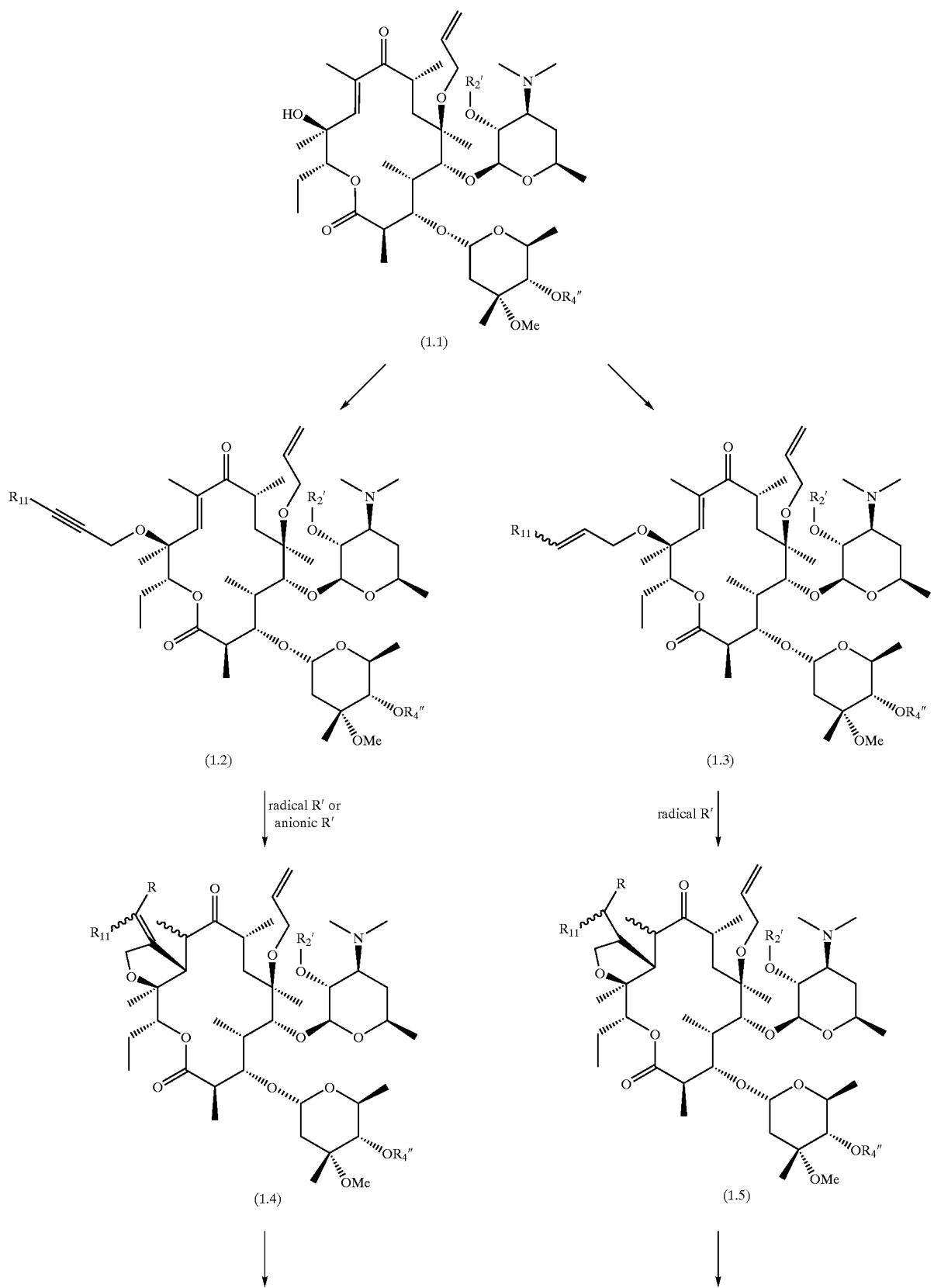

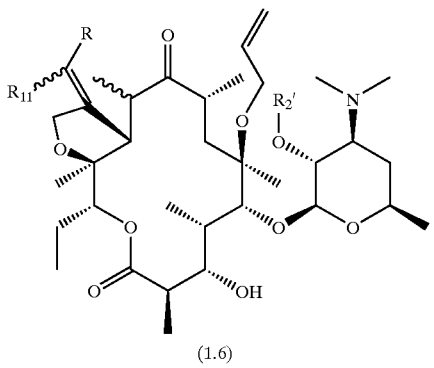

(1.6)

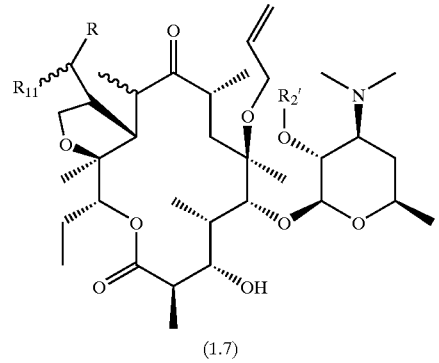

(1.7)

A process of the invention for the preparation of compounds of formula I, as illustrated in Scheme 1, involves preparing compounds of formula (1.4) and (1.5) by a tandem radical or anionic addition and cyclization of compounds of formula (1.2) or (1.3).

Intermediates (1.2) and (1.3) can be prepared by alkylation of the readily available compounds of formula (1.1) which can be prepared according to the process described by Baker et al. *J. Org. Chem.* 1988, 53, 2340–2345; Elliott et al. *J. Med. Chem.* 1988, 41, 1651–1659; Ma et al. *J. Med. Chem.* 2001, 44, 4137–4156, and Or et al. U.S. Pat. 6,075,011-B1. Typical alkylating conditions include treating compounds of formula (1.1) with a suitable alkylating agent, such as propargyl halide, allyl halide, allyl mesylate or the like, in the presence of a base such as $K_2CO_3$, NaOH, NaH, LDA or the like, optionally with a phase transfer catalyst such as tetrabutylammonium iodide, 18-crown-6 or the like, in THF, toluene, methylene chloride, DMF, DMSO, water or the like, or combinations thereof, at from about −50° C. to about 10° C. for 1 hour to 24 hours to provide compounds of formula (1.2) and (1.3). Alternatively, compounds of formula (1.3) can be obtained by reaction of a suitable alkylating agent such as tert-butyl allyl carbonate, tert-butyl 2-butenyl carbonate, allyl acetate, allyl benzoate or the like, in the presence of a palladium catalyst, such as palladium(II) acetate, tetrakis(triphenylphosphine)palladium(0), tris (dibenzylideneacetone)dipalladium(0), tetra (dibenzylideneacetone)dipalladium(0), palladium on carbon or the like, and a suitable phosphine ligand, such as triphenylphosphine, bis(diphenylphosphino)methane, 1,2-bis(diphenylphosphino)ethane, 1,3-bis(diphenylphosphino)propane, 1,4-bis(diphenylphosphino)butane, tri-o-tolylphosphine, or the like, in an aprotic solvent, such as tetrahydrofuran, N,N-dimethylformamide, dimethyl sulfoxide, N-methyl-2-pyrrolidinone, hexamethylphosphoric triamide, 1,2-dimethoxyethane, methyl-tert-butyl ether, heptane, acetonitrile, acetonitrile and ethyl acetate or the like, at from 40° C. to about 150° C. for 0.5 hour to about 48 hours.

In accordance with Scheme 1, compounds of formula I (1.4) and (1.5) of the present invention can be prepared by methods which are well known in the art involving a tandem radical addition and cyclization of intermediates (1.2) and (1.3) with a suitable radical species (R') which can be generated from a radical precursor and an initiator. The radical R' can be centered as, but not limited to, carbon, silicon, tin, oxygen, sulfur, nitrogen, halogen with non-, mono-, di- or tri-substitution depending on the nature of the radical centered atom. A typical radical of this process is selected from, but not limited to, a group consisting of $PhCH_2'$, $Et_3Si$, $(n-Bu)_3Sn.$, tert-BuO., AcS., $PhCH_2CH_2S.$ and Br. A typical radical precursor for this process is selected from, but not limited to, $C_1-C_{12}$ alkyl halide, $C_2-C_6$ alkenyl halide, $C_2-C_6$ alkynyl halide, $C_2-C_6$ alkenyl tri($C_1-C_{12}$ alkyl)stannane, tri($C_1-C_{12}$ alkyl)staniane, hexamethyldistannane, trichlorosilane, triphenylsilane, tert-butyl hydrogen peroxide, thiolacetic acid, phenyl disulfide, N-bromosuccinamide and bromine. A typical radical initiator of this process can be selected from, but not limited to, a group consisting of AIBN, tert-butyl peroxide, benzoyl peroxide. The preferred radical reaction conditions of the present invention includes reacting the compounds of formula (1.2) or (1.3) with a radical generated from a group consisting of, but not limited to, halide, stannane, distannane, silane, mercaptan or disulfide, in the presence of AIBN, optionally in the presence of a reducing agent such as tributylstannane, diphenylsilane, sodium borohydride, magnesium, lithium aluminum hydride or the like, at 40° C. to 1 50° C. for a period of from 1 hour to 10 days, in an aprotic solvents, such as tetrahydrofuran, N,N-dimethylformamide, dimethyl sulfoxide, N-methyl-2-pyrrolidinone, 1,2-dimethoxyethane, methyl-tert-butyl ether, cyclohexane, heptane, acetonitrile, benzene, toluene and ethyl acetate or the like.

Alternatively compounds of formula I (1.4) of the present invention may be prepared by a tandem anionic addition and cyclization of intermediates (1.2) with a suitable anionic species (R) which can be generated from an organometallic precursor. Typically a compound of formula (1.2) is reacted with an organometallic reagents, such as allylmagnesium chloride, methylmagnesium iodide, phenyllithium, triethylaluminum, triethoxysilane, or the like, in the presence of 0–100% molar percent (relative to compound 1.2) of a transitional metal or its salt or its complex such as palladium, iridium, chromium(III) chloride, cerium(III) chloride, palladium(II) acetate, platinum(H) chloride, chloroplatinic acid, nonacabonyliron(0), titanocene (IV) dichloride, bis(1,5-cyclooctadiene)nickel(0), tetrakis (triphenylphosphine)palladium(0) or the like, at −78° C. to 100° C. for a period of from 0.5 to 48 hours, in an aprotic solvents, such as tetrahydrofuran, dimethyl sulfoxide, N-methyl-2-pyrrolidinone, 1,2-dimethoxyethane, methyl-tert-butyl ether, cyclohexane, heptane, acetonitrile, benzene and toluene or the like.

Another process of the invention involves the removal of the cladinose moiety of the compounds of formula I. The cladinose moiety of the macrolide compounds of formulae (1.4) and (1.5) can be removed to give compounds of formulae (1.6) and (1.7) in Scheme 1 by a dilute acid, such as hydrochloric acid, sulfuric acid, perchloric acid, nitric acid, chloroacetic acid, dichloroacetic acid, trifluoroacetic acid and p-toluenesulfonic acid or the like, in a suitable solvent, such as methanol, ethanol, isopropanol, butanol, water or the like, or the mixtures thereof, at 0° C. to about 80° C. for 0.5 hour to 24 hours.

When $R_2''$ is an acyl protecting group, it can be removed upon treatment with methanol at from room temperature to 60° C. When $R_2''$ is a silyl protecting group, the deprotection can be also effected by an acid, such as dilute hydrochloric acid, sulfuric acid, perchloric acid, nitric acid, chloroacetic acid, dichloroacetic acid, trifluoroacetic acid and p-toluenesulfonic acid or the like, or a fluoride, such as tetrabutylammonium fluoride, pyridinium fluoride, ammonium fluoride, hydrofluoric acid or the like, at from 0° C. to 50° C. for 0.5 to 24 hours.

Representative reducing agents include, for example, triphenylphosphine, trimethyl phosphite, thiourea, and dimethyl sulfide or the like. A more thorough discussion of ozonolysis and the conditions therefor can be found in M. B. Smith and J. March "Advanced Organic Chemistry" $5^{th}$ ed., Wiley & Son, Inc, 2001.

An alternative method for the preparation of the ketones (2.1) involves dihydroxylation of the alkene followed by diol cleavage. The glycol (2.2) is prepared by reacting the alkene (1.4), either with stoichiometric amounts of osmium tetraoxide, or with catalytic amounts of osmium tetraoxide if an oxidant such as hydrogen peroxide, tert-butyl hydroperoxide, or N-methylmorpholine-N-oxide is present, in a variety of solvents such as 1,4-dioxane, tetrahydrofuran, tert-butanol, acetone, diethyl ether, water or the like, or the mixture thereof, preferably at from 0° C. to 50° C.

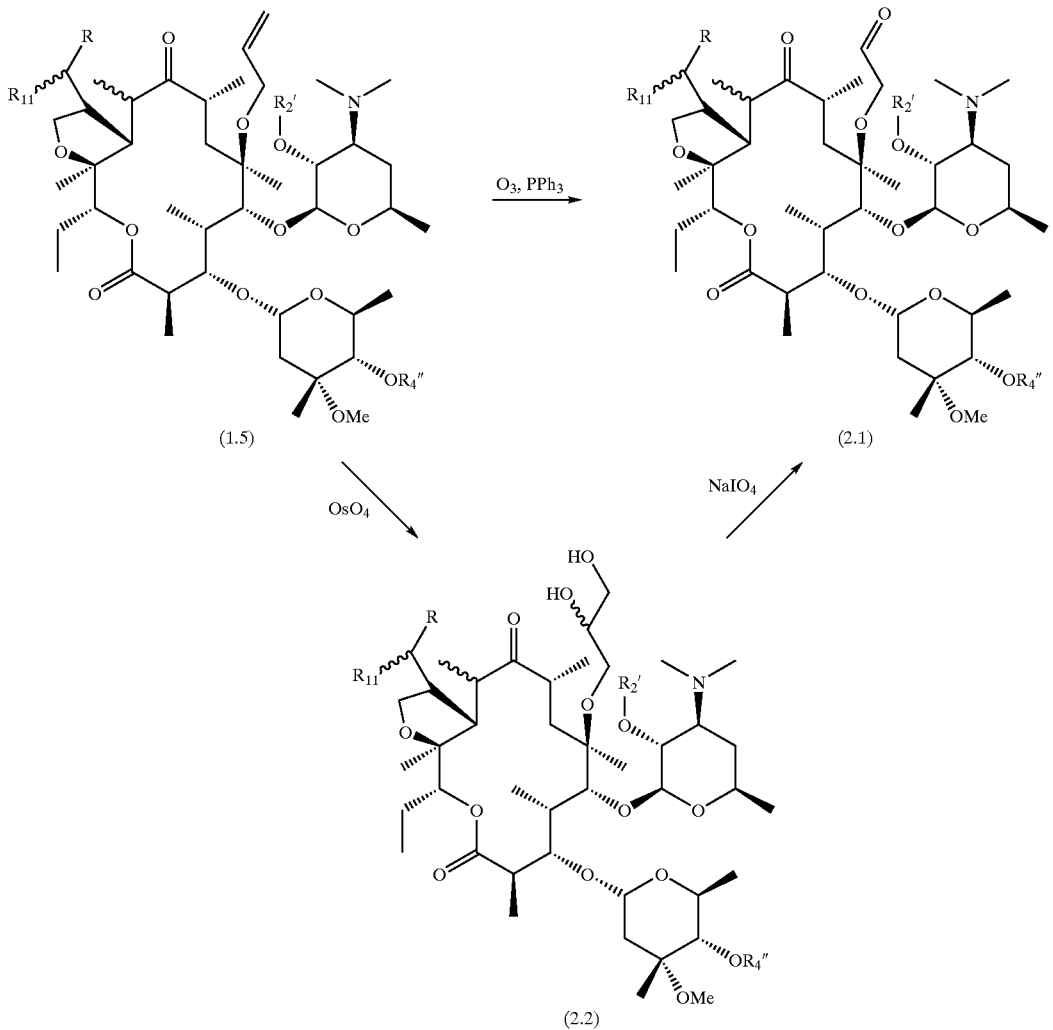

Scheme 2

Conversion of the alkene of formula (1.5) into the ketone (2.1) can be accomplished by exposure of the alkene to ozone followed by decomposition of the ozonide intermediate with an appropriate reducing agent, as outlined in Scheme 2. The reaction is typically carried out in a solvent such as, for example, methanol, ethanol, ethyl acetate, glacial acetic acid, chloroform, methylene chloride or hexanes, or mixtures thereof, at from −78° C. to −20° C.

The glycol (2.2) can be cleaved by a variety of reagents including, but not limited to, periodic acid, lead tetraacetate, manganese dioxide, potassium permanganate, sodium metaperiodate, and N-iodosuccinamide in a variety of solvents such as 1,4-dioxane, tetrahydrofuran, tert-butanol, acetone, ethanol, methanol, water or the like, or the mixture thereof, at from 0° C. to 50° C.

The synthesis of the ketone (2.1) can also be realized in one-pot by reacting the alkene (1.4) with either stoichiometric amounts or catalytic amounts of osmium tetraoxide and a glycol cleavage reagent, such as, for example, periodic acid, lead tetraacetate, manganese dioxide, potassium permanganate, sodium metaperiodate, and N-iodosuccinamide or the like, in a solvent such as 1,4-dioxane, tetrahydrofuran, tert-butanol, acetone, ethanol, methanol, water or the like, or mixtures thereof, at from 0° C. to 50° C.

tetrahydrofuran, 1,2-dimethoxyethane, ethyl acetate, or mixtures thereof, at from 0° C. to 70° C. over a period of 10 minutes to 12 hours. Representative acids include, but are not limited to, hydrochloric acid, phosphoric acid, sulfuric acid, p-toluenesulfonic acid, acetic acid and pyridinium p-toluenesulfonate. Bases which are useful are, for example, triethylamine, pyridine, diisopropylethyl amine, 2,6-lutidine, imidazole and potassium carbonate, and the like. The formation of amines (3.2) can be accomplished by reacting a ketone (2.1) with a primary or secondary amine

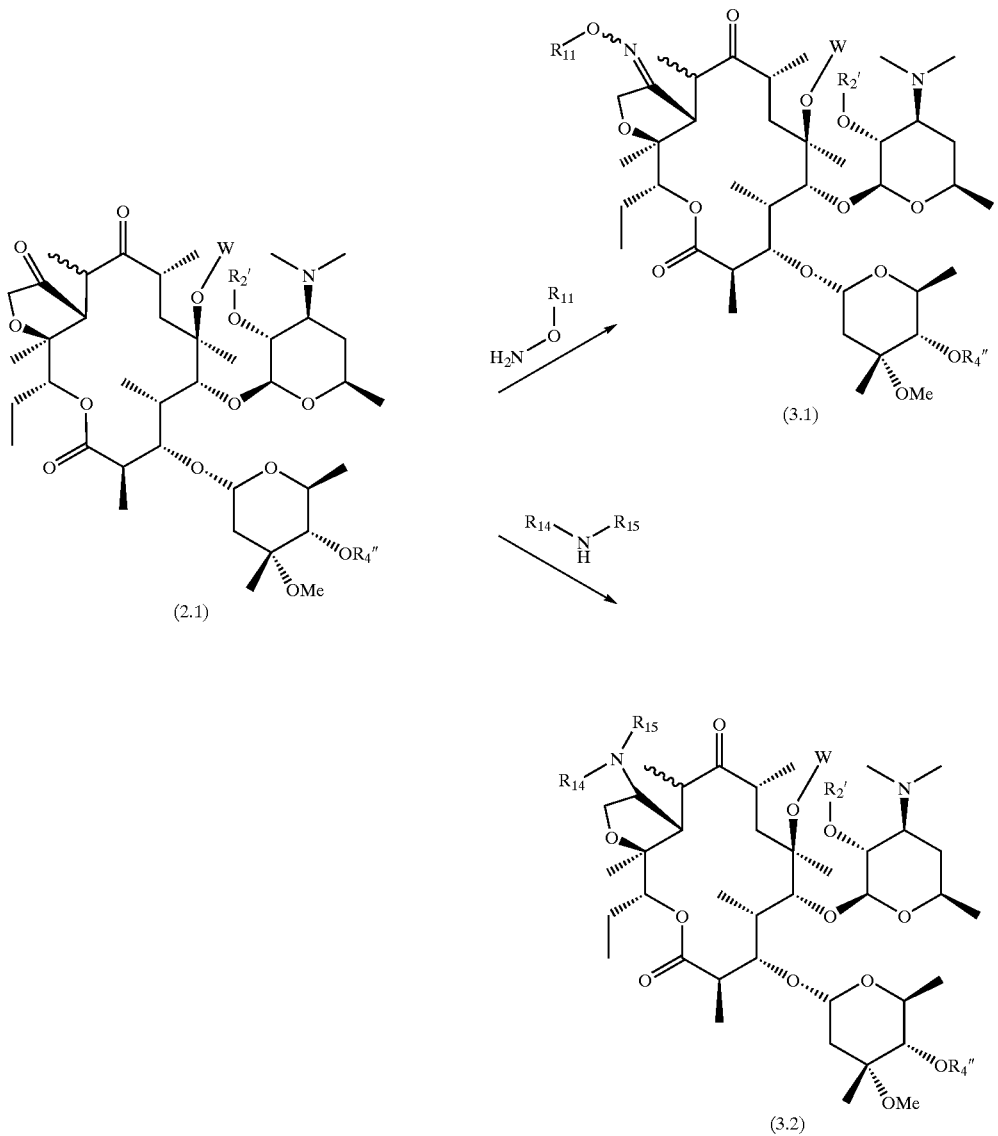

Scheme 3

Compounds of formula (2.1) represent useful intermediates which can be further functionalized in a variety of ways. Scheme 3 details procedures for the conversion of the ketone (2.1) into an oxime of formula (3.1) or an amine of formula (3.2). The formation of oxime (3.1) can be accomplished under either acidic or basic conditions in a variety of solvents such as, for example, methanol, ethanol, water, and a suitable reducing agent such as, for example, hydrogen, sodium borohydride, sodium cyanoborohydride, LAH, zinc, DFBAL-H, triethylsilane, ammonium formate and the like, optionally in the presence of a catalyst such as Raney Ni, palladium on carbon, platinum dioxide, tetrakis (triphenylphosphine)palladium and the like in a suitable solvent such as methanol, acetonitrile, water, tetrahydrofuran, 1,2-dimethoxyethane, ethyl acetate, acetic acid, trifluoroacetic acid, hydrochloric acid or the like, or the mixture thereof, at a pH between 3 and 5 over a period of 5 minutes to 24 hours.

Scheme 4

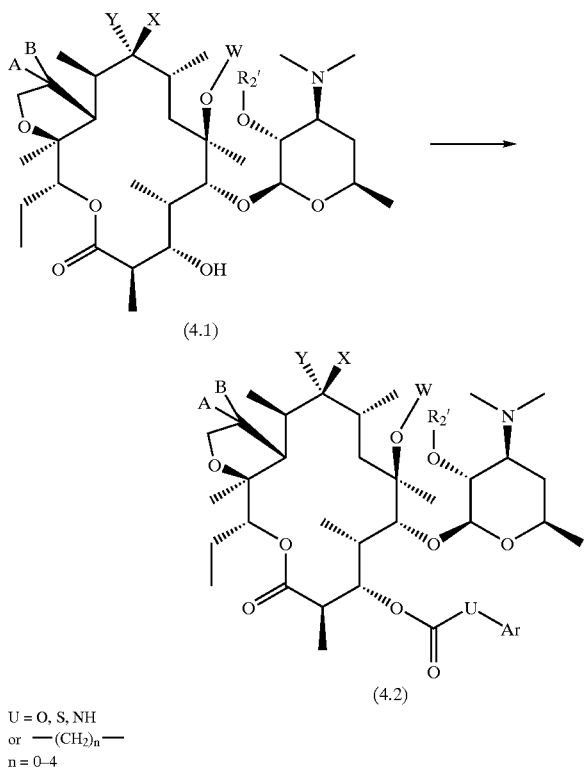

U = O, S, NH
or —(CH$_2$)$_n$—
n = 0–4

Scheme 4 illustrates a procedure for the acylation of the C-3 hydroxyl of compounds of formula (4.1). The hydroxyl group is reacted with an acylating agent such as, but not limited to, acid chlorides, acid anhydrides, and chloroformates in the presence of a base such as pyridine, triethylamine, diisopropyl ethylamine, N-methyl morpholine, N-methyl pyrrolidine, 2,6-lutidine, 1,8-diazabicyclo[5.4.0]undec-7-ene, and DMAP or the like, in an aprotic solvent. For a more extensive discourse on acylating conditions see for example, T. W. Greene and P. G. M. Wuts in "Protective Groups in Organic Synthesis" 3$^{rd}$ ed., John Wiley & Son, Inc, 1999, referred to above herein.

Scheme 5

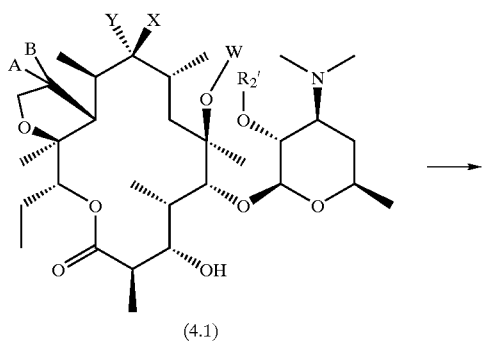

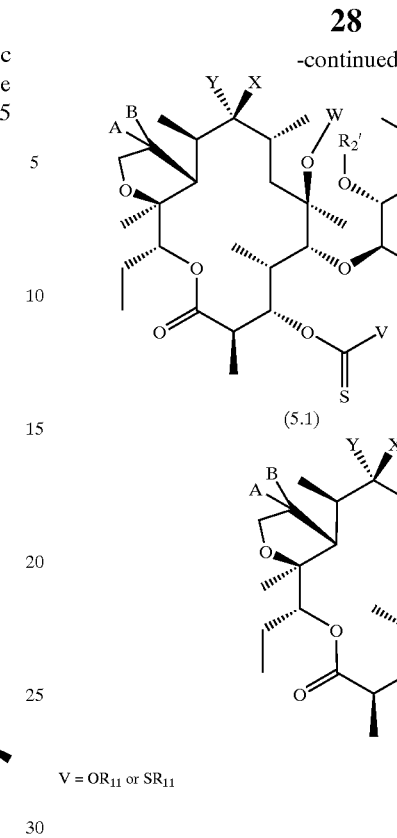

V = OR$_{11}$ or SR$_{11}$

Another process of the invention, as illustrated in Scheme 5, involves the C-3 deoxygenation of the macrolide (4.1) which can be accomplished via a two step procedure shown therein through a xanthate or thiocarbonate of formula (5.1). In the first step, the xanthate is formed by the reaction of alkoxide of alcohol (4.1) with an appropriate thiocarbonyl reagent, such as carbondisulfide followed by methyliodide, or a dithiocarbonyl imidazole; whereas the thiocarbonate can be prepared by the reaction of the alkoxide with either thiocarbonyidiimidazole followed by methanol, ethanol or the like, or a thiochloroformate. One skilled in the art will appreciate that other reagents and conditions exist to perform these transformations and that the examples above are for illustrative purposes only and do not limit the scope of this invention. These reactions are typically run in a polar aprotic solvent, such as tetrahydrofuran, acetonitrile, N,N-dimethylformamide or the like.

In the second step of Scheme 5, the thiocarbonate or xanthate is reduced to give the alkane of formula (5.2). Most typically this is done under radical conditions using, for example, a silane or stannane such as (TMS)$_3$SiH, Ph$_2$SiH$_2$, Bu$_3$SnH, Ph$_3$SnH or the like, and a radical initiator such as AIBN, tert-butyl hydrogen peroxide or the like in an aprotic solvent, such as tetrahydrofuran, N,N-dimethylformamide, dimethyl sulfoxide, N-methyl-2-pyrrolidinone, 1,2-dimethoxyethane, methyl tert-butyl ether, cyclohexane, heptane, acetonitrile, benzene, toluene and ethyl acetate or the like, at 0° C. to 150° C. for a period of from 1 hour to 10 days.

EXAMPLES

The compounds and processes of the present invention will be described further in detail with respect to specific preferred embodiments by way of examples, it being understood that these are intended to be illustrative only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Compound of Formula II: A and B Taken Together With the Carbon Atom to Which They are Attached are C=C$_2$, L is CH$_2$CH$_3$, CH$_2$CH=CH$_2$, X and Y Taken Together With the Carbon Atom to Which They are Attached are C=O, R$_4$" is C(O)CH$_3$ and R$_2$' is H Step 1a. Compound 1.2 of Scheme 1: W is CH$_2$CH=CH$_2$, R$_{11}$ is H, R$_4$" is C(O)CH$_3$ and R$_2$' is C(O)CH$_3$.

A mixture of 2',4"-bis-O-acetyl-6-O-allyl-11-deoxy-10, 11-didehydroerythromycin (640 mg, 0.76 mmol), tetrabutylammonium iodide (56 mg, 0.15 mmol), methylene chloride (4.0 mL), propargyl bromide (80% in toluene, 0.68 mL, 6.09 mmol) and sodium hydroxide (50% in water, 6.0 mL) was stirred at room temperature for 2 hours. The mixture was partitioned (ethtyl acetate and water). The organic phases were washed with water and brine, dried (Na$_2$SO$_4$) and evaporated. The residue was purified by chromatography (silica, hexanes:acetone/95:5 and 3:1) to give 258 mg (39%) of the title compound.

MS (ESI) m/z=878 (M+H)$^+$.

Step 1b. Compound 1.4 of Scheme 1: R and R$_{11}$ Taken Together With the Carbon Atom to Which They are Attached are CHSnBu$_3$, W is CH$_2$CH=CH$_2$, R$_2$' is C(O)CH$_3$ and R$_4$" is C(O)CH$_3$.

A solution of the compound from Step 1a (250 mg, 0.28 mmol) in anhydrous benzene (5.7 mL) was heated to reflux with tributyltin hydride (249 mg, 0.85 mmol) in the presence of AIBN (11.5 mg) for 2 hours before evaporation. The residue was chromatographed (silica, hexanes:acetone/95:5~9:1) to give the title compound (163.5 mg, 49%).

MS (ESI) m/z=1168/1170 (M+H)$^+$.

Step 1c. Compound of Formula I: A and B Taken Together With the Carbon Atom to Which They are Attached are C=CH$_2$, L is CH$_2$CH$_3$, W is CH$_2$CH=CH$_2$, X and Y Taken Together With the Carbon Atom to Which They are Attached are C=O, R$_4$" is C(O)CH$_3$ and R$_2$' is C(O)CH$_3$.

A solution of the compound from Step 1b in ethanol is treated with hydrochloric acid at room temperature for 15 minutes. The mixture is partitioned (ethyl acetate and saturated NaHCO$_3$). The organic phase is washed with water and brine, dried (Na$_2$SO$_4$), evaporated and purified by column chromatography to give the title compound Step 1d. Compound of Formula II: A and B Taken Together With the Carbon Atom to Which They are Attached are C=CH$_2$, L is CH$_2$CH$_3$, W is CH$_2$CH=CH$_2$, X and Y Taken Together With the Carbon Atom to Which They are Attached are C=O, R$_4$" is C(O)CH$_3$ and R$_2$' is H.

A solution of the compound from Step 1c in methanol is refluxed for 24 hours. Evaporated and purified by column chromatography to give the title compound.

Example 2

Compound of Formula II: A and B Taken Together With the Carbon Atom to Which They are Attached are C=CH$_2$, L is CH$_2$CH$_3$, W is CH$_2$CH=CH$_2$, X and Y Taken Together With the Carbon Atom to Which They are Attached are C=O, R$_4$" is H and R$_2$' is H The compound of Example 1 is treated with lithium hydroxide in THF at reflux temperature to provide the title compound.

Example 3

Compound of Formula I: A and B Taken Together With the Carbon Atom to Which They are Attached are C=CH$_2$, L is CH$_2$CH$_3$, W is CH$_2$CH=CH$_2$, X and Y Taken Together With the Carbon Atom to Which They are Attached are C=O, Z is OH and R$_2$' is H Step 3a. Compound of Formula I: A and B Taken Together With the Carbon Atom to Which They are Attached are C=CH$_2$, L is CH$_2$CH$_3$, W is CH$_2$CH=CH$_2$, X and Y Taken Together With the Carbon Atom to Which They are Attached are C=O, Z is OH and R$_2$' is C(O)CH$_3$.

A solution of the compound from Step 1b (163.5 mg, 0.14 mmol) in ethanol (4.0 mL) was treated with hydrochloric acid (2 M, 4.0 mL) at 60° C. for 2 hours before partition (ethyl acetate and saturated NaHCO$_3$). The organic phases were washed with water and brine, dried (Na$_2$SO$_4$) and evaporated. The residue was purified by chromatography (silica, hexanes:acetone/95:5~4:1) to give the title compound (60.3 mg, 63%) as one of the C10 stereoisomers.

MS (ESI) m/z=680 (M+H)$^+$. $^{13}$C NMR (125 MHz, CDCl$_3$): δ 215.7, 174.7, 145.8, 136.4, 116.3, 112.1, 100.1, 86.2, 81.1, 79.7, 77.6, 77.4, 71.6, 70.7, 68.8, 64.6, 63.5, 48.7, 45.4, 44.3, 40.6, 37.3, 36.5, 35.9, 31.3, 22.0, 21.1, 20.4, 19.5, 15.5, 15.3, 14.8, 10.5, 8.1.

Step 3b. Compound of Formula I: A and B Taken Together With the Carbon Atom to Which They are Attached are C=CH$_2$, L is CH$_2$CH$_3$, W is CH,CH=CH$_2$, X and Y Taken Together With the Carbon Atom to Which They are Attached are C=O, Z is OH and R$_2$' is H.

A solution of the compound of Step 3a in methanol is refluxed for 24 hours, evaporated and purified by column chromatography to give the title compound.

Example 4

Compound of Formula I: A and B Taken Together With the Carbon Atom to Which They are Attached are C=CH$_2$, L is CH$_2$CH$_3$, W is CH$_2$CH=CH$_2$, X and Y Taken Together With the Carbon Atom to Which They are Attached are C=O, Z is OH, and R$_2$' is H Step 4a. Compound of Formula I: A and B Taken Together With the Carbon Atom to Which They are Attached are C=CH$_2$, L is CH$_2$CH$_3$, W is CH$_2$CH=CH, X and Y Taken Together With the Carbon Atom to Which They are Attached are C=O, Z is OH, and R$_2$' is C(O)CH$_3$.

A solution of the compound from Step 1b (163.5 mg, 0.14 mmol) in ethanol (4.0 mL) was treated with hydrochloric acid (2 M, 4.0 mL) at 60° C. for 2 hours before partition (ethyl acetate and saturated NaHCO$_3$). The organic phases were washed with water and brine, dried (Na$_2$SO$_4$) and evaporated. The residue was purified by chromatography (silica, hexanes:acetone/95:5~4:1) to give the title compound (24.9 mg, 26%) as one of the C10 stereoisomers.

MS (ESI) m/z=680 (M+H)$^+$. $^{13}$C NMR (125 MHz, CDCl$_3$): δ 215.8, 176.7, 152.3, 136.3, 115.2, 107.6, 104.0, 92.2, 86.1, 80.8, 77.2, 72.1, 69.2, 64.7, 64.6, 61.8, 51.1, 48.4, 44.6, 40.8, 39.3, 38.1, 34.8, 29.7, 21.4, 21.2, 20.9, 19.8, 19.6, 15.4, 10.9, 10.7, 8.1.

Step 4b. Compound of Formula I: A and B Taken Together With the Carbon Atom to Which They are Attached are C=CH$_2$, L is CH$_2$CH$_3$, W is CH$_2$CH=CH$_3$, X and Y Taken Together With the Carbon Atom to Which They are Attached are C=O, Z is OH and R$_2$' is H.

A solution of the compound of Step 4a in methanol is refluxed for 24 hours, evaporated and purified by column chromatography to give the title compound.

Example 5

Compound of Formula II: A and B Taken Together With the Carbon Atom to Which They are Attached are C=$CH_2$, L is $CH_2CH_3$, W is $CH_2CH(O)$, X and Y Taken Together With the Carbon Atom to Which They are Attached are C=O, $R_2'$ is H, and $R_4''$ is H Step 5a. Compound of Formula II: A and B Taken Together With the Carbon Atom to Which They are Attached are C=$CH_2$, L is $CH_2C_3$, W is $CH_2CH(O)$, X and Y Taken Together With the Carbon Atom to Which They are Attached are C=O, $R_2'$ is Ac, and $R_4''$ is Ac.

To a solution of the compound of Example 2 in aqueous acetone at 25° C. is added $OsO_4$ (5 mol %) followed by $NaIO_4$ (4 equivalents) and the mixture is stirred for 4–6 hours. The reaction mixture is diluted with EtOAc and is washed with aqueous $NaHCO_3$, brine and dried over $Na_2SO_4$. Removal of the solvents in vacuo provides the title compound.

Step 5b. Compound of formula II: A and B Taken Together With the Carbon Atom to Which They are Attached are C=$CH_2$, L is $CH_2CH_3$, W is $CH_2CH(O)$, X and Y Taken Together With the Carbon Atom to Which They are Attached are C=O, $R_2'$ is H, and $R_4''$ is H.

The compound of Step 5a is treated with methanol at 25° C. for 24 hours or at refluxing temperature for 24 hours and evaporated to give the title compound.

Example 6

Compound of formula II: A and B Taken Together With the Carbon Atom to Which They are Attached are C=$CH_2$, L is $CH_2CH_3$, W is $CH_2C\equiv CH$, X and Y Taken Together With the Carbon Atom to Which They are Attached are C=O, $R_2'$ is H, and $R_4''$ is H Step 6a. Compound of Formula II: A and B Taken Together With the Carbon Atom to Which They are Attached are C=$CH_2$, L is CH2$CH_3$, W is $CH_2C\equiv CH$, X and Y Taken Together With the Carbon Atom to Which They are Attached are C=O, $R_2'$ is Ac, and $R_4''$ is Ac.

The compound of Step 5a of Example 5 is treated with an excess of phosphonium Wittig reagent according to the literature procedures (a.). *Tetrahedron Lett.*, 1999, 40(49), 8575–8578. (b). *Synlett.*, 1996, (6), 521–522.) to provide the title compound.

Step 6b. Compound of Formula II: A and B Taken Together With the Carbon Atom to Which They are Attached are C=$CH_2$, L is $CH_2H_3$, W is $CH_2C\equiv CH$, X and Y Taken Together With the Carbon Atom to Which They are Attached are C=O, $R_2'$ is Ac, and $R_4''$ is Ac.

The compound of Step 6a is treated with methanol at 25° C. for 24 hours or at refluxing temperature for 2–4 hours and evaporated to provide the title compound.

Example 7

Compound of formula II: A and B Taken Together With the Carbon Atom to Which They are Attached are C=$CH_2$, L is $CH_2CH_3$, W is $CH_2C\equiv C$-(3-Quinolyl), X and Taken Together With the Carbon Atom to Which They are Attached are C=O, $R_2'$ is H, and $R_4''$ is H A mixture of a compound of Example 6 (1 equivalent) and Pd(PPh$_3$)$_2$Cl$_2$ (0.02 equivalents) in 5:1 acetonitrile:triethylamine is degassed and flushed with nitrogen, treated sequentially with CuI (0.01 equivalents) and 3-bromoquinoline (2–3 equivalents), stirred at room temperature for 10 minutes, heated at 70° C. for 6–24 hours, diluted with ethyl acetate and washed sequentially with water and brine and dried ($Na_2SO_4$) to provide the title compound.

Example 8

Compound of formula II: A and B Taken Together With the Carbon Atom to Which They are Attached are C=$CH_2$, L is $CH_2CH_3$, W is $CH_2CH_2NHCH_2$-(4-Chlorophenyl), X and Y Taken Together With the Carbon Atom to Which They are Attached are C=O, $R_2'$ is H, and $R_4''$ is H To a solution of the compound from Example S in methanol is added 4-chlorobenzylamine, excess $NaBH_3CN$ and enough acetic acid to give a pH 4 at room temperature. The reaction mixture is stirred at room temperature for 4–8 hours, cooled to 0° C., neutralized with a solution of saturated aqueous $Na_2CO_3$ and extracted with $CH_2Cl_2$. The organic layer is dried over $Na_2SO_4$, evaporated and purified by column chromatography on silica gel to provide the title compound.

The compounds of Examples 9 through 26 may be prepared according to the procedures described in Examples 1 through 8 and the synthetic schemes and discussions contained herein.

Example 9

Compound of formula II: A and B Taken Together With the Carbon Atom to Which They are Attached are C=$CH_2$, L is $CH_2CH_3$, W is $CH_2CH_2NCH_3CH_2$-Phenyl, X and Y Taken Together With the Carbon Atom to Which They are Attached are C=O, $R_2'$ is H, and $R_4''$ is H

Example 10

Compound of formula II: A and B Taken Together With the Carbon Atom to Which They are Attached are C=$CH_2$, L is $CH_2CH_3$, W is $CH_2CH_2NCH_3CH_2$-(2-Pyridyl), X and Y Taken Together With the Carbon Atom to Which They are Attached are C=O, $R_2'$ is H, and $R_4''$ is H

Example 11

Compound of formula II: A and B Taken Together With the Carbon Atom to Which They are Attached are C=$CH_2$, L is $CH_2CH_3$, W is $CH_2CH_2NCH_3CH_2$-(3-Pyridyl), X and Y taken together with the carbon atom to which they are attached are C=O, $R_2'$ is H, and $R_4''$ is H

Example 12

Compound of Formula II: A and B Taken Together With the Carbon Atom to Which They are Attached are C=$CH_2$, L is $CH_2CH_3$, W is $CH_2CH_2NCH_3CH_2$-(3-Quinolyl), X and Y Taken Together With the Carbon Atom to Which They are Attached are C=O, $R_2'$ is H, and $R_4''$ is H

Example 13

Compound of Formula II: A and B Taken Together With the Carbon Atom to Which They are Attached are C=$CH_2$, L is $CH_2CH_3$, W is $CH_2CH=CH$-Phenyl, X and Y Taken Together With the Carbon Atom to Which They are Attached are C=O, $R_2'$ is H, and $R_4''$ is H

Example 14

Compound of Formula II: A and B Taken Together With the Carbon Atom to Which They are Attached are C=$CH_2$, L is $CH_2CH_3$, W is $CH_2CH=CH$-(2-Pyridyl), X and Y Taken Together With the Carbon Atom to Which They are Attached are C=O, $R_2'$ is H, and $R_4''$ is H

Example 15

Compound of Formula II: A and B Taken Together With the Carbon Atom to Which They are Attached are $C=CH_2$, L is $CH_2CH_3$, W is $CH_2CH=CH$-(3-Pyridyl), X and Y Taken Together With the Carbon Atom to Which They are Attached are C=O, $R_2'$ is H, and $R_4''$ is H

Example 16

Compound of Formula II: A and B Taken Together With the Carbon Atom to Which They are Attached are $C=CH_2$, L is $CH_2CH_3$, W is $CH_2CH=CH$-(3-(5-Cyano)pyridyl), X and Y Taken Together With the Carbon Atom to Which They are Attached are C=O, $R_2'$ is H, and $R_4''$ is H

Example 17

Compound of Formula II: A and B Taken Together With the Carbon Atom to Which They are Attached are $C=CH_2$, L is $CH_2CH_3$, W is $CH_2CH=CH$-(6-(Aminocarbonyl)-3-quinolyl), X and Y Taken Together With the Carbon Atom to Which They are Attached are C=O, $R_2'$ is H, and $R_4''$ is H

Example 18

Compound of Formula II: A and B Taken Together With the Carbon Atom to Which They are Attached are $C=CH_2$, L is $CH_2CH_3$, W is $CH_2C\equiv C$-Phenyl, X and Y Taken Together With the Carbon Atom to Which They are Attached are C=O, $R_2'$ is H, and $R_4''$ is H

Example 19

Compound of Formula II: A and B Taken Together With the Carbon Atom to Which They are Attached are $C=CH_2$, L is $CH_2CH_3$, W is $CH_2C\equiv C$-(2-Pyridyl), X and Y Taken Together With the Carbon Atom to Which They are Attached are C=O, $R_2'$ is H, and $R_4''$ is H

Example 20

Compound of Formula II: A and B Taken Together With the Carbon Atom to Which They are Attached are $C=CH_2$, L is $CH_2CH_3$, W is $CH_2C\equiv C$-(3-Pyridyl), X and Y Taken Together With the Carbon Atom to Which They are Attached are C=O, $R_2'$ is H, and $R_4''$ is H

Example 21

Compound of Formula II: A and B Taken Together With the Carbon Atom to Which They are Attached are $C=CH_2$, L is $CH_2CH_3$, W is $CH_2C\equiv C$-(3-(5-Cyano)pyridyl), X and Y Taken Together With the Carbon Atom to Which They are Attached are C=O, $R_2'$ is H, and $R_4''$ is H

Example 22

Compound of Formula II: A and B Taken Together With the Carbon Atom to Which They are Attached are $C=CH_2$, L is $CH_2CH_3$, W is $CH_2C\equiv C$-(5-(2-Pyridyl)-2-thienyl), X and Y Taken Together With the Carbon Atom to Which They are Attached are C=O, $R_2'$ is H, and $R_4''$ is H

Example 23

Compound of Formula II: A and B Taken Together With the Carbon Atom to Which They are Attached are $C=CH_2$, L is $CH_2CH_3$, W is $CH_2C\equiv C$-(5-(3-Pyridinyl)-2-pyrrolyl), X and Y Taken Together With the Carbon Atom to Which They are Attached are C=O, $R_2'$ is H, and $R_4''$ is H

Example 24

Compound of Formula II: A and B Taken Together With the Carbon Atom to Which They are Attached are $C=CH_2$, L is $CH_2CH_3$, W is $CH_2C\equiv C$-(5-(2-Pyrimidyl)-2-thienyl), X and Y Taken Together With the Carbon Atom to Which They are Attached are C=O, $R_2'$ is H, and $R_4''$ is H

Example 25

Compound of Formula II: A and B Taken Together With the Carbon Atom to Which They are Attached are $C=CH_2$, L is $CH_2CH_3$, W is $CH_2C\equiv C$-(5-(2-Pyrazinyl)-2-pyrrolyl), X and Y Taken Together With the Carbon Atom to Which They are Attached are C=O, $R_2'$ is H, and $R_4'$ is H

Example 26

Compound of Formula II: A and B Taken Together With the Carbon Atom to Which They are Attached are $C=CH_2$, L is $CH_2CH_3$, W is $CH_2C\equiv C$-(6-Quinolyl), X and Y Taken Together With the Carbon Atom to Which They are Attached are C=O, $R_2'$ is H, and $R_4''$ is H Although the invention has been described in detail with respect to various preferred embodiments it is not intended to be limited thereto, but rather those skilled in the art will recognize that variations and modifications may be made therein which are within the spirit of the invention and the scope of the appended claims.

What is claimed is:

1. A compound represented by the formula

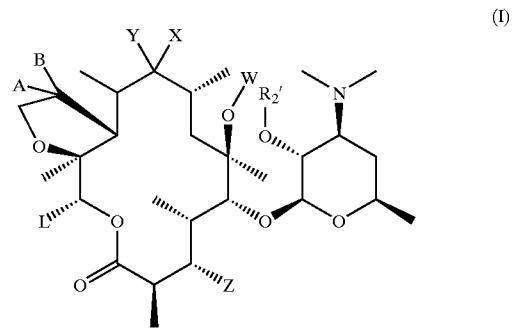

(I)

or a pharmaceutically acceptable salts, esters or prodrug thereof wherein

A is selected from:
   (a) —OH;
   (b) —$OR_p$, where $R_p$ is a hydroxy protecting group;
   (c) —$R_1$, where $R_1$ is selected from:
      1. aryl;
      2. substituted aryl;
      3. heteroaryl; or
      4. substituted heteroaryl;
   (d) —$OR_1$, where $R_1$ is as previously defined;
   (e) —$R_2$, where $R_2$ is selected from:
      1. hydrogen;
      2. halogen;
      3. $C_1$–$C_6$ alkyl containing 0, 1, 2, or 3 heteroatoms selected O, S and N, optionally substituted with one or more substituents selected from halogen, cyano, oxo, aryl, substituted aryl, heteroaryl, and substituted heteroaryl;
4. $C_2$–$C_6$ alkenyl containing 0, 1, 2, or 3 heteroatoms selected from O, S and N, optionally substituted with one or more substituents selected from halogen, cyano, oxo, aryl, substituted aryl, heteroaryl, and substituted heteroaryl; or
5. $C_2$–$C_6$ alkynyl containing 0, 1, 2, or 3 heteroatoms selected from O, S and N, optionally substituted with one or more substituents selected from halogen, cyano, oxo, aryl, substituted aryl, heteroaryl, and substituted heteroaryl;
(f) —$OR_2$, where $R_2$ is previously defined;
(g) —$S(O)_nR_{11}$, where n=0, 1 or 2, and $R_{11}$ is selected from hydrogen, $R_1$ and $R_2$, where $R_1$ and $R_2$ are as previously defined;
(h) —$OC(O)R_{11}$, where $R_{11}$ is as previously defined;
(i) —$C(O)R_{11}$, where $R_{11}$ is as previously defined;
(j) —$C(O)NHR_{11}$, where $R_{11}$ is as previously defined;
(k) —$OC(O)NHR_{11}$, where $R_{11}$ is as previously defined;
(l) —$NHC(O)R_{11}$, where $R_{11}$ is as previously defined;
(m) —$NHC(O)NHR_{11}$, where $R_{11}$ is as previously defined;
(n) —$NHS(O)_nR_{11}$, where n and $R_{11}$ are as previously defined;
(o) —$NR_{14}R_{15}$, where $R_{14}$ and $R_{15}$ are each independently $R_{11}$, where $R_{11}$ is as previously defined; or
(p) —$NHR_3$, where $R_3$ is an amino protecting group;
B is selected from:
(a) hydrogen;
(b) deuterium;
(c) —CN;
(d) —$NO_2$;
(e) halogen;
(f) —OH;
(g) —$R_1$, where $R_1$ is as previously defined;
(h) —$R_2$, where $R_2$ is as previously defined; or
(i) —$OR_p$, where $R_p$ is as previously defined;
provided that when B is halogen, —$NO_2$, —OH or $OR_p$, A is $R_1$ or $R_2$;
or, alternatively, A and B taken together with the carbon atom to which they are attached are selected from:
(a) C=O;
(b) $C(OR_2)_2$, where $R_2$ is as previously defined;
(c) $C(SR_2)_2$, where $R_2$ is as previously defined;
(d) $C(OR_{12})(OR_{13})$, where $R_{12}$ and $R_{13}$ taken together are —$(CH_2)_m$—, and where m=2 or 3;
(e) $C(SR_{12})(SR_{13})$, where $R_{12}$ and $R_{13}$ taken together are —$(CH_2)_m$— and where m is as previously defined;
(f) C=$CR_{11}R_{14}$, where $R_{11}$ and $R_{14}$ are as previously defined;
(g) C=N—O—$R_{11}$, where $R_{11}$ is as previously defined;
(h) C=$NNHR_{11}$, where $R_{11}$ is as previously defined;
(i) C=$NNHC(O)R_{11}$, where $R_{11}$ is as previously defined;
(j) C=N=$CR_{11}R_{14}$, where $R_{11}$ and $R_{14}$ are as previously defined;
(k) C=$NNHC(O)NHR_{11}$, where $R_{11}$ is as previously defined;
(l) C=$NNHS(O)_nR_{11}$, where n and $R_{11}$ are as previously defined;
(m) C=$NNHR_3$, where $R_3$ is as previously defined; or
(n) C=$NR_{11}$, where $R_{11}$ is as previously defined;

one of X and Y is hydrogen and the other is selected from:
(a) hydrogen;
(b) deuterium;
(c) —OH;
(d) —$OR_p$, where $R_p$ is as previously defined; or
(e) —$NR_4R_5$, where $R_4$ and $R_5$ are each independently selected from:
1. hydrogen;
2. $C_1$–$C_{12}$ alkyl, optionally substituted with one or more substituents selected from halogen, cyano, aryl, substituted aryl, heteroaryl and substituted heteroaryl; or
$R_4$ and $R_5$, taken together with the nitrogen atom to which they are attached form a 3–10 membered heteroalkyl ring containing 0–2 additional hetero atoms selected from O, S and N;
or alternatively, X and Y taken together with the carbon atom to which they are attached are selected from:
(a) C=O;
(b) C=$NR_{11}$, where $R_{11}$ is as previously defined;
(c) C=$NC(O)R_{11}$, where $R_{11}$ is as previously defined;
(d) C=N—$OR_6$, where $R_6$ is selected from:
1. hydrogen;
2. —$CH_2O(CH_2)_2OCH_3$,
3. —$CH_2O(CH_2O)_nCH_3$, where n is as previously defined;
4. —$C_1$–$C_{12}$ alkyl, optionally substituted with one or more substituents selected from the group consisting of halogen, cyano, aryl, substituted aryl, heteroaryl and substituted heteroaryl;
5. $C_3$–$C_{12}$ cycloalkyl;
6. C(O)—$C_1$–$C_{12}$ alkyl;
7. C(O)—$C_3$–$C_{12}$ cycloalkyl;
8. C(O)—$R_1$, where $R_1$ is as previously defined; or
9. —$Si(R_a)(R_b)(R_c)$, wherein $R_a$, $R_b$ and $R_c$ are each independently selected from $C_1$–$C_{12}$ alkyl, aryl and substituted aryl; or
(e) C=N—O—$C(R_7)(R_8)$—O—$R_6$, where $R_6$ is as previously defined, provided that $R_6$ is not C(O)—$C_1$–$C_{12}$ alkyl, C(O)—$C_3$–$C_{12}$ cycloalkyl, or C(O)—$R_1$; and $R_7$ and $R_8$ taken together with the carbon atom to which they are attached form a $C_3$–$C_{12}$ cycloalkyl group or each is independently selected from:
1. hydrogen; or
2. $C_1$–$C_{12}$ alkyl;
L is selected from:
(a) —$CH(OH)CH_3$;
(b) $C_1$–$C_6$ alkyl, optionally substituted with one or more substituents selected from halogen, cyano, aryl, substituted aryl, heteroaryl, and substituted heteroaryl;
(c) $C_2$–$C_6$ alkenyl, optionally substituted with one or more substituents selected from halogen, cyano, aryl, substituted aryl, heteroaryl, and substituted heteroaryl; or
(d) $C_2$–$C_6$ alkynyl, optionally substituted with one or more substituents selected from halogen, cyano, aryl, substituted aryl, heteroaryl, and substituted heteroaryl;
W is selected from:
(a) $C2C_6$ alkyl containing 0, 1, 2, or 3 heteroatoms selected from O, S and N, optionally substituted with one or more substituents selected from halogen, cyano, oxo, aryl, substituted aryl, heteroaryl, and substituted heteroaryl;
(b) $C_2$–$C_6$ alkenyl containing 0, 1, 2, or 3 heteroatoms selected from O, S and N, optionally substituted with one or more substituents selected from halogen, cyano, oxo, aryl, substituted aryl, heteroaryl, and substituted heteroaryl; or (c) $C_2$–$C_6$ alkynyl containing 0, 1, 2, or 3 heteroatoms selected from O, S and N, optionally substituted with one or more substituents selected from halogen, cyano, oxo, aryl, substituted aryl, heteroaryl, and substituted heteroaryl;

Z is selected from:
(a) hydrogen;
(b) —OH;
(c) —$OR_p$, where $R_p$ is as previously defined;
(d) —$OR_{11}$, where $R_{11}$ is as previously defined;
(e) —$OC(O)R_{11}$, where $R_{11}$ is as previously defined;
(f) —$OC(O)NHR_{11}$, where $R_{11}$ is as previously defined;
(g) —$S(O)_nR_{11}$, where n and $R_{11}$ are as previously defined; or
(h) —

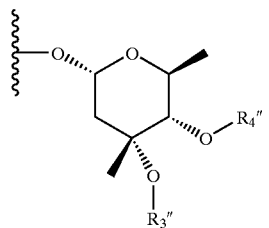

where $R_3''$ is hydrogen or methyl; $R_4''$ is hydrogen or $R_p$, where $R_p$ is as previously defined; and $R_2'$ is hydrogen or $R_p$, where $R_p$ is as previously defined.

2. A compound according to claim 1 which is represented by the formula

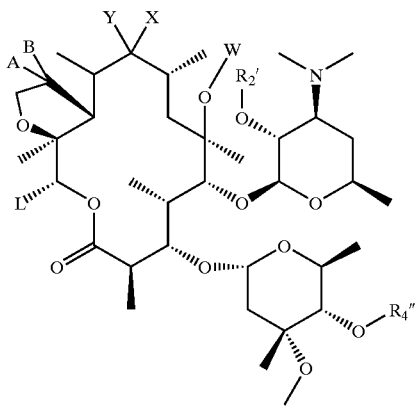

(II)

wherein A, B, L, W, X, Y, $R_4''$ and $R_2'$ are as defined in claim 1.

3. A compound according to claim 1 wherein L is ethyl and A, B, W, X, Y, Z and $R_2'$ are as defined in claim 1.

4. A compound according to claim 1 of formula I, wherein L is ethyl, X and Y taken together with the carbon atom to which they are attached are C=O, and A, B, W, Z and $R_2'$ are as defined in claim 1.

5. A compound according to claims 1 or 2 which is selected from:

Compound of formula II: A and B taken together with the carbon atom to which they are attached are C=$CH_2$, L is $CH_2CH_3$, W is $CH_2CH=CH_2$, X and Y taken together with the carbon atom to which they are attached are C=O, $R_4''$ is $C(O)CH_3$, and $R_2'$ is H;

Compound of formula II: A and B taken together with the carbon atom to which they are attached are C=$CH_2$, L is $CH_2CH_3$, W is $CH_2CH=CH_2$, X and Y taken together with the carbon atom to which they are attached are C=O, $R_4''$ is H and $R_2'$ is H;

Compound of formula I: A and B taken together with the carbon atom to which they are attached are C=$CH_2$, L is $CH_2CH_3$, W is $CH_2CH=CH_2$, X and Y taken together with the carbon atom to which they are attached are C=O, Z is OH and $R_2'$ is H;

Compound of formula I: A and B taken together with the carbon atom to which they are attached are C=$CH_2$, L is $CH_2CH_3$, W is $CH_2CH=CH_2$, X and Y taken together with the carbon atom to which they are attached are C=O, Z is OH and $R_2'$ is H;

Compound of formula II: A and B taken together with the carbon atom to which they are attached are C=$CH_2$, L is $CH_2CH_3$, W is $CH_2CH(O)$, X and Y taken together with the carbon atom to which they are attached are C=O, $R_2'$ is H, and $R_4''$ is H;

Compound of formula II: A and B taken together with the carbon atom to which they are attached are C=$CH_2$, L is $CH_2CH_3$, W is $CH_2C\equiv CH$, X and Y taken together with the carbon atom to which they are attached are C=O, $R_2'$ is H, and $R_4''$ is H;

Compound of formula II: A and B taken together with the carbon atom to which they are attached are C=$CH_2$, L is $CH_2CH_3$, W is $CH_2C\equiv C$-(3-quinolyl), X and Y taken together with the carbon atom to which they are attached are C=O, $R_2'$ is H, and $R_4''$ is H;

Compound of formula II: A and B taken together with the carbon atom to which they are attached are C=$CH_2$, L is $CH_2CH_3$, W is $CH_2CH_2NHCH_2$-(4-chlorophenyl), X and Y taken together with the carbon atom to which they are attached are C=O, $R_2'$ is H, and $R_4''$ is H;

Compound of formula II: A and B taken together with the carbon atom to which they are attached are C=$CH_2$, L is $CH_2CH_3$, W is $CH_2CH_2NCH_3CH_2$-phenyl, X and Y taken together with the carbon atom to which they are attached are C=O, $R_2'$ is H, and $R_4''$ is H;

Compound of formula II: A and B taken together with the carbon atom to which they are attached are C=$CH_2$, L is $CH_2CH_3$, W is $CH_2CH_2NCH_3CH_2$-(2-pyridyl), X and Y taken together with the carbon atom to which they are attached are C=O, $R_2'$ is H, and $R_4''$ is H;

Compound of formula II: A and B taken together with the carbon atom to which they are attached are C=$CH_2$, L is $CH_2CH_3$, W is $CH_2CH_2NCH_3CH_2$-(3-pyridyl), X and Y taken together with the carbon atom to which they are attached are C=O, $R_2'$ is H, and $R_4''$ is H;

Compound of formula II: A and B taken together with the carbon atom to which they are attached are C=$CH_2$, L is $CH_2CH_3$, W is $CH_2CH_2NCH_3CH_2$-(3-quinolyl), X and Y taken together with the carbon atom to which they are attached are C=O, $R_2'$ is H, and $R_4''$ is H;

Compound of formula II: A and B taken together with the carbon atom to which they are attached are C=$CH_2$, L is $CH_2CH_3$, W is $CH_2CH=CH$-phenyl, X and Y taken together with the carbon atom to which they are attached are C=O, $R_2'$ is H, and $R_4''$ is H;

Compound of formula II: A and B taken together with the carbon atom to which they are attached are C=$CH_2$, L is $CH_2CH_3$, W is $CH_2CH=CH$-(2-pyridyl), X and Y taken together with the carbon atom to which they are attached are C=O, $R_2'$ is H, and $R_4''$ is H;

Compound of formula II: A and B taken together with the carbon atom to which they are attached are C=CH$_2$, L is CH$_2$CH$_3$, W is CH$_2$CH=CH-(3-pyridyl), X and Y taken together with the carbon atom to which they are attached are C=O, R$_2$' is H, and R$_4$" is H;

Compound of formula II: A and B taken together with the carbon atom to which they are attached are C=CH$_2$, L is CH$_2$CH$_3$, W is CH$_2$CH=CH-(3-(5-cyano)pyridyl), X and Y taken together with the carbon atom to which they are attached are C=O, R$_2$' is H, and R$_4$" is H;

Compound of formula II: A and B taken together with the carbon atom to which they are attached are C=CH$_2$, L is CH$_2$CH$_3$, W is CH$_2$CH=CH-(6-(aminocarbonyl)3-quinolyl), X and Y taken together with the carbon atom to which they are attached are C=O, R$_2$' is H, and R$_4$" is H;

Compound of formula II: A and B taken together with the carbon atom to which they are attached are C=CH$_2$, L is CH$_2$CH$_3$, W is CH$_2$C≡C-phenyl, X and Y taken together with the carbon atom to which they are attached are C=O, R$_2$' is H, and R$_4$" is H;

Compound of formula II: A and B taken together with the carbon atom to which they are attached are C=CH$_2$, L is CH$_2$CH$_3$, W is CH$_2$C≡C-(2-pyridyl), X and Y taken together with the carbon atom to which they are attached are C=O, R$_2$' is H, and R$_4$" is H;

Compound of formula II: A and B taken together with the carbon atom to which they are attached are C=CH$_2$, L is CH$_2$CH$_3$, W is CH$_2$C≡C-(3-pyridyl), X and Y taken together with the carbon atom to which they are attached are C=O, R$_2$' is H, and R$_4$" is H;

Compound of formula II: A and B taken together with the carbon atom to which they are attached are C=CH$_2$, L is CH$_2$CH$_3$, W is CH$_2$C≡C-(3-(5-cyano)pyridyl), X and Y taken together with the carbon atom to which they are attached are C=O, R$_2$' is H, and R$_4$" is H;

Compound of formula II: A and B taken together with the carbon atom to which they are attached are C=CH$_2$, L is CH$_2$CH$_3$, W is CH$_2$C≡C-(5-(2-pyridyl)-2-thienyl), X and Y taken together with the carbon atom to which they are attached are C=O, R$_2$' is H, and R$_4$" is H;

Compound of formula II: A and B taken together with the carbon atom to which they are attached are C=CH$_2$, L is CH$_2$CH$_3$, W is CH$_2$C≡C-(5-(3-pyridinyl)-2-pyrroly)), X and Y taken together with the carbon atom to which they are attached are C=O, R$_2$' is H, and R$_4$" is H;

Compound of formula II: A and B taken together with the carbon atom to which they are attached are C=CH$_2$, L is CH$_2$CH$_3$, W is CH$_2$C≡C-(5-(2-pyrimidyl)-2-thienyl), X and Y taken together with the carbon atom to which they are attached are C=O, R$_2$' is H, and R$_4$" is H;

Compound of formula II: A and B taken together with the carbon atom to which they are attached are C=CH$_2$, L is CH$_2$CH$_3$, W is CH$_2$C≡C-(5-pyrazinyl)-2-pyrrolyl), X and Y taken together with the carbon atom to which they are attached are C=O, R$_2$' is H, and R$_4$" is H; or Compound of formula II: A and B taken together with the carbon atom to which they are attached are C=CH$_2$, L is CH$_2$CH$_3$, W is CH$_2$C≡C-(6-quinolyl), X and Y taken together with the carbon atom to which they are attached are C=O, R$_2$' is H, and R$_4$" is H.

6. A pharmaceutical composition comprising a therapeutically effective amount of a compound of claim 1, or a pharmaceutically-acceptable salt, ester or prodrug thereof, in combination with a pharmaceutically acceptable carrier.

7. A method for controlling a bacterial infection in an animal comprising administering to an animal in need of such treatment a therapeutically-effective amount of a pharmaceutical composition according to claim 6.

8. A method for the preparation of a compound of Formula I as defined in claim 1 wherein A and B taken together with the carbon atom to which they are attached are C=CR$_{11}$R$_{14}$, where L, W, W Y, Z, R$_2$', R$_{11}$ and R$_{14}$ are as defined in claim 1 comprising reacting a compound represented by the formula

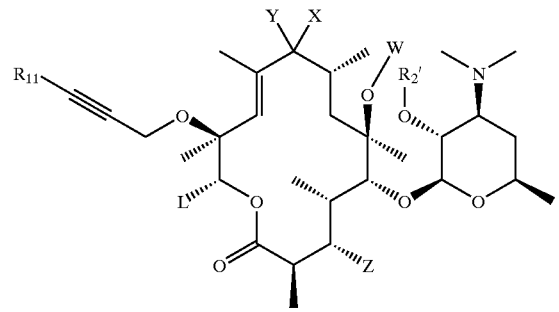

where L, W, X, Y, Z, R$_2$' and R$_{11}$ are as previously defined, with a radical species in the presence of 2,2'-azobisisobutyronitrile, optionally in the presence of a reducing agent in an aprotic solvent at from about 40° C. to about 150° C. for from 2 hours to 10 days to provide a compound of Formula I, wherein A and B taken together with the carbon atom to which they are attached are C=CR$_{11}$R$_{14}$, and where L, W, X, Y, Z, R$_2$', R$_{11}$ and R$_{14}$ are as defined in claim 1.

9. A method for preparing a compound according to claim 1 of formula I where A is hydrogen and B is —CHR$_{11}$R$_{14}$, and where L, W, X, Y, Z, R$_2$', R$_{11}$ and R$_{14}$ are as defined in claim 1 comprising i) reacting a compound represented by the formula

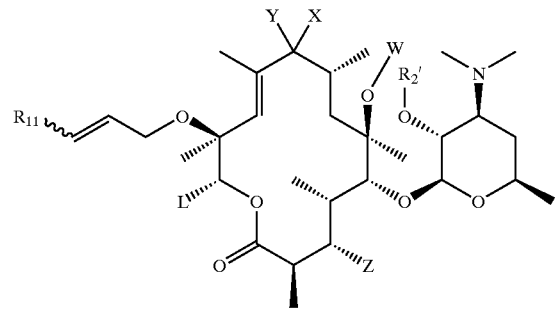

where L, W, X, Y, Z, R$_2$' and R$_{11}$ are as previously defined, with a radical species in the presence of 2,2'-azobisisobutyronitrile, optionally in the presence of a reducing agent in an aprotic solvent at from about 40° C. to about 150° C. for from 2 hours to 10 days to provide a compound of formula I, wherein A is hydrogen, B is —CHR$_{11}$R$_{14}$, and where L, W, X, Y, Z, R$_2$', R$_{11}$ and R$_{14}$ are as defined in claim 1.

* * * * *